US009404875B2

(12) United States Patent
Langeveld

(10) Patent No.: US 9,404,875 B2
(45) Date of Patent: Aug. 2, 2016

(54) METHOD AND SYSTEM FOR EXTRACTING SPECTROSCOPIC INFORMATION FROM IMAGES AND WAVEFORMS

(71) Applicant: Rapiscan Systems, Inc., Torrance, CA (US)

(72) Inventor: Willem G. J. Langeveld, Menlo Park, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 184 days.

(21) Appl. No.: 14/228,340

(22) Filed: Mar. 28, 2014

(65) Prior Publication Data
US 2014/0341340 A1  Nov. 20, 2014

Related U.S. Application Data

(63) Continuation of application No. 12/850,595, filed on Aug. 4, 2010, now Pat. No. 8,724,774.

(60) Provisional application No. 61/231,048, filed on Aug. 4, 2009.

(51) Int. Cl.
*G01N 23/06* (2006.01)
*G01N 23/087* (2006.01)

(52) U.S. Cl.
CPC ............ *G01N 23/063* (2013.01); *G01N 23/087* (2013.01)

(58) Field of Classification Search
CPC ................... G06T 7/0012; G06T 2207/10081; G06T 2207/10116; G06T 2200/04; A61B 6/4035; A61B 6/4042
See application file for complete search history.

(56) References Cited

U.S. PATENT DOCUMENTS

| | | |
|---|---|---|
| 3,417,243 A | 12/1968 | Hill |
| 4,020,346 A | 4/1977 | Dennis |
| 4,366,382 A | 12/1982 | Kotowski |

(Continued)

FOREIGN PATENT DOCUMENTS

| | | |
|---|---|---|
| EP | 0549858 | 3/1998 |
| WO | 9909400 | 2/1999 |

(Continued)

OTHER PUBLICATIONS

International Search Report for PCT/US2010/044475, mailed on Oct. 29, 2010, Rapiscan Laboratories Inc.

(Continued)

*Primary Examiner* — Hoon Song
(74) *Attorney, Agent, or Firm* — Novel IP

(57) ABSTRACT

The application discloses systems and methods for determining an atomic number of a material being scanned by generating a predetermined number of transmission data samples, determining a variance of the transmission data samples, and determining the atomic number of the material being scanned by comparing the variance or a derivative of the variance of the transmission data samples to one or more predetermined variances. The application also discloses systems and methods for determining an atomic number of a material being scanned by deriving transmission signal samples of the material being scanned, determining a variance of the signal samples, and determining an atomic number of the material being scanned by comparing the variance of the signal samples, or a derivative of the variance, to one or more predetermined variances.

11 Claims, 21 Drawing Sheets

(56) References Cited

U.S. PATENT DOCUMENTS

| | | |
|---|---|---|
| 5,958,299 A | 9/1999 | Kury et al. |
| 6,069,936 A | 5/2000 | Bjorkholm |
| 6,632,020 B2 | 10/2003 | Kaufhold et al. |
| 7,440,544 B2 | 10/2008 | Scheinman et al. |
| 7,512,210 B2 | 3/2009 | Possin et al. |
| 7,522,696 B2 | 4/2009 | Imai |
| 7,702,075 B2 | 4/2010 | Wang et al. |
| 7,920,735 B2 | 4/2011 | Krauss et al. |
| 8,111,889 B2 | 2/2012 | Basu et al. |
| 8,724,774 B2 | 5/2014 | Langeveld |
| 2003/0072417 A1 | 4/2003 | Kaufhold |
| 2005/0152504 A1 | 7/2005 | Shih |
| 2005/0226484 A1 | 10/2005 | Basu |
| 2007/0286329 A1 | 12/2007 | Wang |
| 2008/0013672 A1 | 1/2008 | Krauss |
| 2008/0240341 A1 | 10/2008 | Possin |
| 2011/0123084 A1* | 5/2011 | Sebok .................. G06K 9/3216 382/132 |

FOREIGN PATENT DOCUMENTS

| | | |
|---|---|---|
| WO | 2005084351 | 9/2005 |
| WO | WO 2011/017475 | 2/2011 |

OTHER PUBLICATIONS

Supplementary Partial European Search Report for EP2462431, Nov. 17, 2014.

Supplementary European Search Report for Application No. EP10807126, dated Feb 6, 2015.

\* cited by examiner

METHOD AND SYSTEM FOR EXTRACTING SPECTROSCOPIC INFORMATION FROM IMAGES AND WAVEFORMS

CROSS-REFERENCE

The present application is as continuation of U.S. patent application Ser. No. 12/850,595, entitled "Method and System for Extracting Spectroscopic Information from Images and Waveforms" and filed on Aug. 4, 2010, which relies on U.S. Patent Provisional No. 61/231,048, entitled "Method and System for Extracting Spectroscopic Information from Images and Waveforms" and filed on Aug. 4, 2009, for priority.

All of the above-mentioned applications are herein incorporated by reference in their entirety.

FIELD OF THE INVENTION

The present invention relates to security systems. More particularly, the present invention relates to using variances in detected X-ray signals to generate spectroscopic information. Still more particularly, the spectroscopic information is interpreted to determine the identity of a material based on its atomic number.

BACKGROUND

Conventional X-ray imaging systems comprise an X-ray source and an array of detectors. Some or all of the X-rays produced in the X-ray source fall on the detector array after passing through an object being scanned such as baggage or cargo. Commonly used X-ray cargo inspection systems use a pulsed linear-accelerator-based X-ray source, which emits a Bremsstrahlung spectrum of X-rays. The X-rays that penetrate the cargo are detected by detectors that usually consist of scintillator crystals (e.g. $CdWO_4$) with photodiode readouts. During typical pulse durations of a few microseconds, tens to hundreds of thousands of X-rays arrive at each detector, except for those that are absorbed or scattered by the cargo.

The spectrum of X-rays arriving at the detectors after passing through the cargo material being scanned possesses different characteristics with respect to different materials. In other words, the resultant spectrum of X-rays is material specific. Lower-energy X-rays are absorbed more readily in the cargo than higher-energy ones mainly due to the photoelectric effect. High-energy X-rays can also be lost, mainly due to Compton scattering and electron-positron pair-production. The cross sections for these processes, a measure of their probability, depend on the energy of the X-rays and on the atomic number (Z) of the cargo material. In particular, the cross section for pair-production increases with the Z of the material. Therefore, after X-rays have traversed high-Z materials, the energy of the remaining X-rays is, on average, lower than after they have traversed equivalent quantities of lower-Z materials: relatively, more X-rays at the high end of the spectrum are lost.

Hence, it is possible to determine the type of material traversed by the X-rays if the spectrum of the X-rays arriving in the detectors is measured with sufficient precision. Spectroscopic techniques may, in principle, be used for measurement of the energy spectrum of the X-rays. Minimum count rates for standard systems with pulsed X-ray sources, for example count rates at "air value" (where there is nothing in the X-ray beam), are typically on the order of several to tens of millions of X-rays per second, for a low dose configuration but can be as high as several to tens of billions of X-rays per second in high energy, high-dose systems. Therefore, the X-ray count rates are usually too high to be measured using standard spectroscopy methods, where the energy of each arriving X-ray is measured individually.

Further, the scintillation detectors usually employed in conventional X-ray scanning systems are much too slow. For example, $CdWO_4$ has a ~15 μsec decay time, which is longer than the typical X-ray pulse itself. Hence, the detector would be unable to detect separate signals for each of the many individual X-rays arriving in the same pulse. Therefore, X-ray detectors used in most radiography applications function by measuring the total X-ray energy transmitted, as opposed to the energies of individual X-rays detected. This is sometimes called "operating in integration mode".

Hence, there is need for a method of detecting the presence of materials based on their atomic numbers by spectroscopic analysis in a manner that takes advantage of the information provided by discrete X-ray transmissions, yet can be implemented by conventional detector systems.

SUMMARY OF THE INVENTION

In one embodiment, the present invention is a method for determining an atomic number of a material being scanned. In one embodiment, the present invention generates a predetermined number of transmission data samples by obtaining a plurality of X-ray transmission measurements of the material being scanned. In one embodiment, the method of the present invention is employed to determine a variance of the transmission data samples. In one embodiment of the present invention, the atomic number of the material being scanned is determined by comparing the variance or a derivative of the variance of the transmission data samples to one or more predetermined variances.

In one embodiment, the methods of the present invention are able to use a value dependent upon, and derived from, characteristics of individual, discrete X-rays and not simply rely on the calculations of total transmitted, and detected, energy.

In one embodiment, the present invention is a method for determining an atomic number of a material being scanned, the method comprising deriving a plurality of transmission signal samples of the material being scanned. In one embodiment, the transmission signal samples are generated from a plurality of time slices of an X-ray pulse and collectively generate a waveform. In one embodiment, the variance of the signal samples of the material being scanned is determined. In one embodiment, the atomic number of the material being scanned is determined by comparing the variance of the signal samples, or a derivative of the variance, to one or more predetermined variances.

In one embodiment, the one or more predetermined variances are derived by generating waveforms of a plurality of reference materials, wherein a portion of said plurality of reference materials has high atomic numbers and wherein a portion of said plurality of reference materials has low atomic numbers.

In one embodiment, the variance of the signal samples in the waveform of high atomic number material is lower than the variance of the signal samples in the waveform of low atomic number material.

In one embodiment, the method of the present invention also includes averaging values from pixels corresponding to the same object across at least one X-ray transmission image.

In one embodiment, the said plurality of transmission signal samples are generated using transmission detectors comprising plastic scintillator material.

In another embodiment, the said plurality of transmission signal samples are generated using transmission detectors comprising Cerium-doped Lutetium Yttrium Orthosilicate (LYSO).

In one embodiment, the present invention is an X-ray inspection system for determining an atomic number of a material being scanned, comprising a source of X-ray radiation, a plurality of detectors, and a processing unit. In one embodiment, the processing unit is adapted to generate a predetermined number of transmission data samples by obtaining from said detectors a plurality of X-ray transmission measurements of the material being scanned. In one embodiment, the processing unit is adapted to determine a variance of the transmission data samples. In one embodiment, the processing unit is capable of determining the atomic number of the material being scanned by comparing the variance or a derivative of the variance of the transmission data samples to one or more predetermined variances.

In another embodiment, the present invention is an X-ray inspection system for determining an atomic number of a material being scanned, comprising a source of X-ray radiation; a plurality of detectors; and a processing unit. In one embodiment, the processing unit is adapted to derive a plurality of transmission signal samples of the material being scanned, wherein said transmission signal samples are obtained from said plurality of detectors, generated from a plurality of time slices of an X-ray pulse and collectively define a waveform. In one embodiment, the processing unit is adapted to determine a variance of the signal samples of the material being scanned. In one embodiment, the processing unit is adapted to determine an atomic number of the material being scanned by comparing the variance of the signal samples, or a derivative of the variance, to one or more predetermined variances.

In one embodiment of the system of the present invention, the one or more predetermined variances are stored in memory and derived by generating transmission data samples of a plurality of reference materials. In one embodiment, a portion of said plurality of reference materials has high atomic numbers and a portion of said plurality of reference materials has low atomic numbers.

In one embodiment of the system of the present invention, the derivative of variance is a noise figure determined by dividing the variance in the transmission data samples by a mean transmission value.

In one embodiment of the system of the present invention, the variance in the transmission data samples taken of high atomic number material is lower than the variance in the transmission data samples taken of low atomic number material.

In one embodiment of the system of the present invention, the processing unit is further adapted to take an average of values from pixels corresponding to the same object across multiple X-ray transmission images.

In one embodiment of the system of the present invention, the detectors comprise X-ray detectors that have a fast response time compared to the X-ray pulse duration, such as fast scintillators (e.g. plastic scintillator, LYSO, $LaBr_3$, or other fast scintillators) or fast solid-state detectors (e.g., CZT, or TlBr, or other fast semiconductor-based X-ray detectors).

In another embodiment, the present invention is a method for determining an atomic number of a first material and a second material, wherein the first material is concealed using the second material. In one embodiment, the method of the present invention comprises obtaining at least one X-ray transmission image of the first material and second material. In one embodiment, the method of the present invention comprises determining a transmission value, representing the second material, from pixels that represent part of the second material in the at least one image. In one embodiment, the method further comprises determining a transmission value and variance, representing both the first material and the second material, from pixels that represent the image of both the first material and the second material. In one embodiment, the method further comprises obtaining a transmission value, representing air, without material present. In one embodiment, the method further comprises determining a transmission value, representing the first material, using the transmission value representing the second material, the transmission value representing both the first material and the second material, and the transmission value representing air. In one embodiment, the method further comprises determining a noise variable representing the first material. In one embodiment, the method further comprises determining an atomic number of the first material by comparing the noise variable corresponding to the first material with a reference value. In one embodiment, the noise variable is determined based upon the variance representing both the first material and second material and the transmission value representing the first material.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

The present invention is directed towards a method for performing Noise Spectroscopy (NS) to obtain spectroscopic information in a statistical fashion. The present invention is further directed towards analysis of spectral information to achieve discrimination of materials based on their atomic number (Z). In particular, this allows detection of materials having a high atomic number, including Special Nuclear Materials (SNM). The methods of the present invention do not require special X-ray sources (e.g. dual-energy) or additional detector arrays, and can facilitate material discrimination and/or detection of SNM in near real time. It should further be appreciated that the present system can be implemented in existing X-ray systems by providing a processing unit or controller having a processor configured to execute, and a memory storing, a plurality of programmatic instructions capable of performing the functional steps described herein.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In a conventional X-ray source, in order to produce X-rays, electrons are accelerated to a particular energy, and directed towards a target, which is usually made from a material having a high atomic number such as tungsten. The electrons may be accelerated by using a conventional linear accelerator (LINAC). The electrons interact with the atoms of the target material and produce X-rays primarily by the Bremsstrahlung process. These X-rays emerge from the target material with a particular energy spectrum, which is known as a Bremsstrahlung spectrum because of the manner in which it was produced.

Figure 1A:
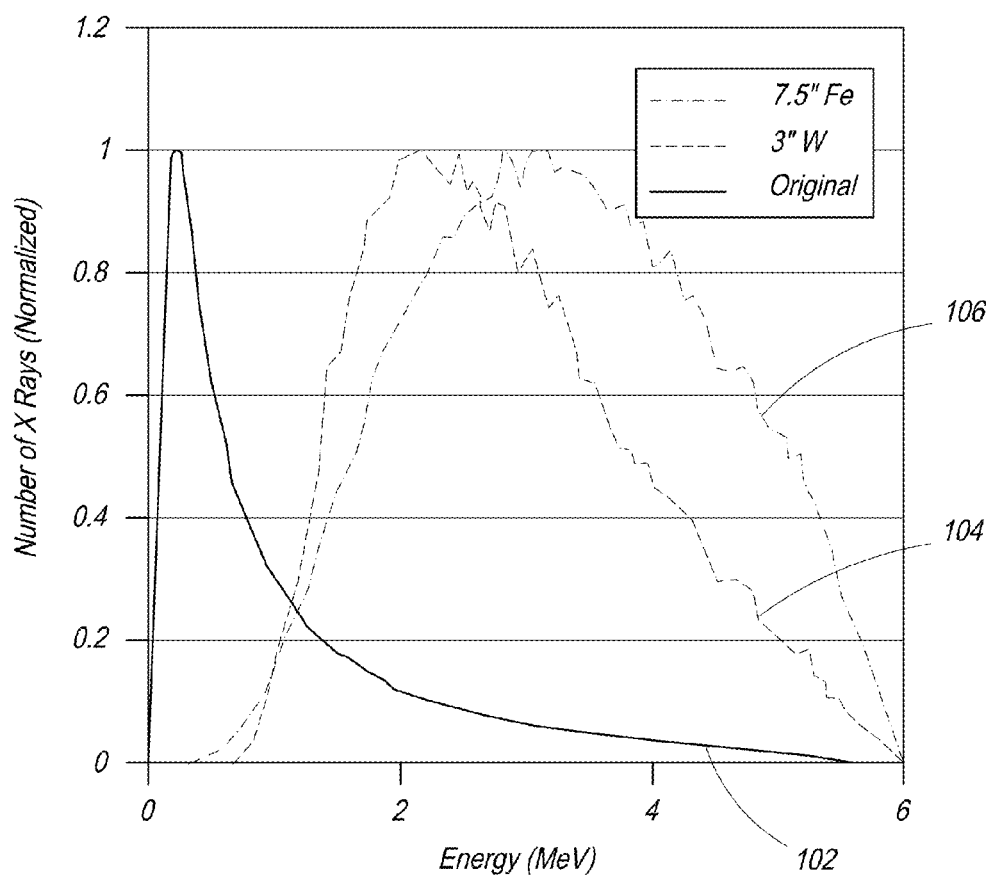
FIG. 1A illustrates a Bremsstrahlung spectrum produced by an electron beam having an energy of 6 MeV as simulated using the Electron Gamma Shower (EGS) Monte Carlo electron-gamma transport code and the spectra that result after the X-rays pass through steel and tungsten.

FIG. 1A illustrates a Bremsstrahlung spectrum 102 produced by an electron beam with an energy of 6 MeV simulated using the Electron Gamma Shower (EGS) Monte Carlo electron-gamma transport code. Dashed line 104 illustrates the spectrum of X-rays that result after passing through three inches of tungsten. Dotted line 106 illustrates the spectrum of X-rays that result after passing through 7.5 inches of steel. The spectra are normalized so that the peak value equals one. When the X-rays pass through one or more objects such as cargo being scanned, they interact with the materials of the objects. The X-rays that remain after passing through the cargo deposit either some or all of their energy in a detector array that is placed at a suitable location, or miss the detector array altogether if their direction was sufficiently altered by the cargo.

A number of different phenomena may take place due to the interaction of the X-rays with the cargo materials. For example, at low energies, the photoelectric effect, where an X-ray knocks a bound electron from an orbit of an atom, is predominant. In certain cases, Rayleigh scattering, which occurs when an X-ray is elastically deflected by the coherent effects of the electric field of the electrons in the cargo materials, may occur. At higher energies, Compton scattering, where an X-ray is deflected by a single electron in the cargo material, occurs most dominantly. At even higher energies, electron-positron pair production occurs. In this process, the X-ray creates an electron-positron pair in the electric field of the nucleus of an atom of the cargo material. In certain cases electron-positron pairs may be created in the field of the electrons of an atom of the cargo material, with a smaller cross section. Also, the X-rays can interact directly with the nuclei of an atom of the cargo material in photonuclear reactions. These reactions happen predominantly in materials having a high atomic number, and are most probable at approximately 15 million electron volt (MeV) X-ray energy.

Figure 1B:
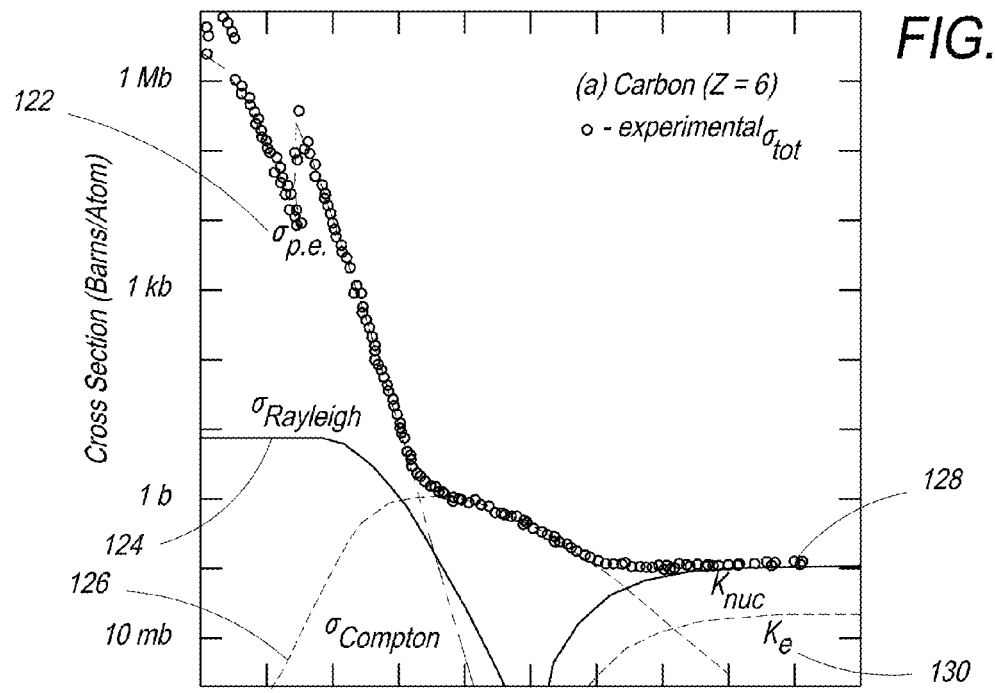
FIG. 1B illustrates the photoelectric effect cross section ($\sigma_{p.e.}$), the Rayleigh and Compton effect cross sections ($\sigma_{Rayleigh}$ and $\sigma_{Compton}$), the pair-production cross sections in the nuclear and electron fields ($\kappa_{nuc}$ and $\kappa_e$), corresponding to carbon which has a low atomic number (Z=6)

FIG. 1B illustrates the photoelectric effect cross section ($\sigma_{p.e.}$) 122, the Rayleigh and Compton effect cross sections ($\sigma_{Rayleigh}$ and $\sigma_{Compton}$), 124 and 126, respectively, the pair-production cross sections in the nuclear and electron fields ($\kappa_{nuc}$ and $\kappa_e$), 128 and 130, respectively, corresponding to carbon, which has a low atomic number (Z=6).

Figure 1C:
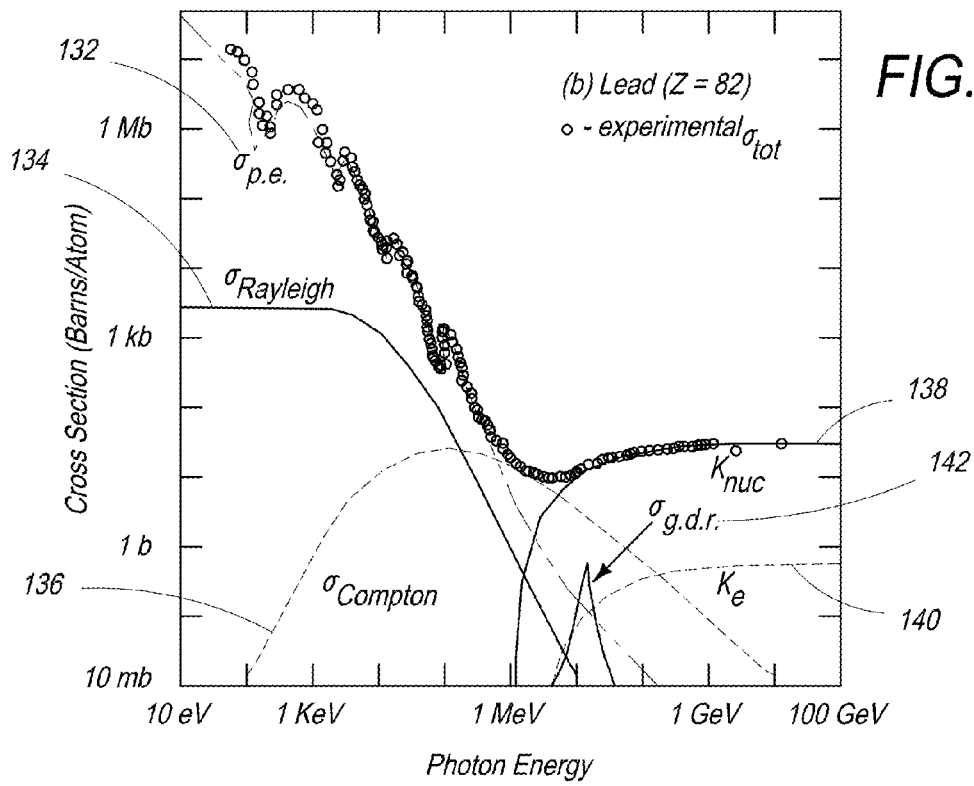
FIG. 1C illustrates the photoelectric effect cross section ($\sigma_{p.e.}$), the Rayleigh and Compton effect cross sections ($\sigma_{Rayleigh}$ and $\sigma_{Compton}$), the pair-production cross sections in the nuclear and electron fields ($\kappa_{nuc}$ and $\kappa_e$) and the photonuclear (giant-dipole-resonance) cross section ($\sigma_{g.d.r.}$), corresponding to lead which has a high atomic number (Z=82)

FIG. 1C illustrates the photoelectric effect cross section ($\sigma_{p.e.}$) 132, the Rayleigh and Compton effect cross sections ($\sigma_{Rayleigh}$ and $\sigma_{Compton}$), 134 and 136, respectively, the pair-production cross sections in the nuclear and electron fields ($\kappa_{nuc}$ and $\kappa_e$), 138 and 140, respectively, and the photonuclear (giant-dipole-resonance) cross section ($\sigma_{g.d.r.}$), 142, corresponding to lead, which has a high atomic number (Z=82).

As illustrated in FIGS. 1B and 1C, the photoelectric effect causes low-energy X-rays to be greatly attenuated for both low-atomic number as well as high atomic number materials. This leads to beam hardening: as the beam of X-rays passes through the material, low-energy X-rays are preferentially removed from the beam and the mean energy of the remaining X-rays increases. FIGS. 1B and 1C also illustrate that the overall cross section of the X-rays interacting with the cargo material depends on the atomic number of the material. In particular, the electron-positron pair-production cross section is much higher for materials having a high atomic number than that for materials having a low atomic number. Since the pair-production process is only effective at higher X-ray energies, it leads to a greater loss of high-energy X-rays in materials having a high atomic number than in materials having a low atomic number.

Referring back to FIG. 1A, solid line 102 in the graph represents a Bremsstrahlung spectrum produced by a beam of X-rays having 6 MeV energy in a theoretical setup. The beam of X-rays is projected towards a slab of steel (Fe), having a thickness of 7.5 inches, which is a material having a relatively low atomic number (Z=26). The spectrum of X-rays arriving at a detector located behind the steel slab is illustrated by using a dotted line, shown as 106 in FIG. 1A. In another case, the beam of X-rays is projected towards a slab of 3 inches of tungsten (W), which is a material having a relatively high atomic number (Z=72). The spectrum of X-rays arriving at a detector behind the W slab is illustrated by using a dashed line, shown as 104 in FIG. 1A. The respective slab thicknesses of 3 inches and 7.5 inches are chosen to provide, approximately, the same transmission of total X-ray energy through the slabs as measured in the detector. It is observed that the X-rays below ~1 MeV are almost all dispersed because of the photoelectric effect. The mean energy of the X-rays remaining after passing through the tungsten, $\mu(W)$, is 2.85 MeV, which is considerably lower than the mean energy of the X-rays remaining after passing through the steel, $\mu(Fe)$, which equals 3.32 MeV. The squares of these quantities are $\mu^2(W)$=8.12 MeV$^2$ and $\mu^2(Fe)$=11.02 MeV$^2$. The means of the squares of the energies are: $<E^2(W)>$=9.24 MeV$^2$ and $<E^2(Fe)>$=12.32 MeV$^2$, and the square roots of these quantities are $\sqrt{<E^2(W)>}$=3.04 MeV and $\sqrt{<E^2(Fe)>}$=3.51 MeV. These values are only slightly higher than $\mu(W)$ and $\mu(Fe)$, respectively. Angle brackets < > are used to designate taking the average.

The variances for the two distributions are calculated as:
$\sigma^2(W)$<$E^2(W)$>−$\mu^2(W)$=1.12 MeV$^2$; and
$\sigma^2(Fe)$=<$E^2(Fe)$>−$\mu^2(Fe)$=1.30 MeV$^2$.

The spreads (or standard deviations) are:
$\sigma(W)$=1.06 MeV; and
$\sigma(Fe)$=1.14 MeV.

As illustrated in FIG. 1A, the shape of the spectrum behind tungsten is lopsided, with a skew towards lower energies, peaking at about 2.2 MeV, which is well below the mean energy (2.85 MeV). On the other hand, the shape of the spectrum behind steel is more symmetric, peaking at about 3.1 MeV, considerably closer to the mean energy (3.32 MeV). Further, the medians of the two spectra, i.e. 2.67 MeV behind tungsten and 3.25 MeV behind steel, are even more different than the means (2.85 and 3.32 MeV).

The results provided above are only exemplary. In general, similar results are obtained for other X-ray beam energies (above about 4 MeV) produced by using a LINAC, and for other slab thicknesses and different materials having low or high atomic numbers. Yet more generally (e.g., also below about 4 MeV), the energy spectrum of the X-rays detected after passing through a material is different from the incident energy spectrum in a material-specific manner. The present invention provides a method for determining the type of material traversed by the X-rays by analyzing and measuring properties of the spectrum of the X-rays arriving in the detectors.

Figure 2A:
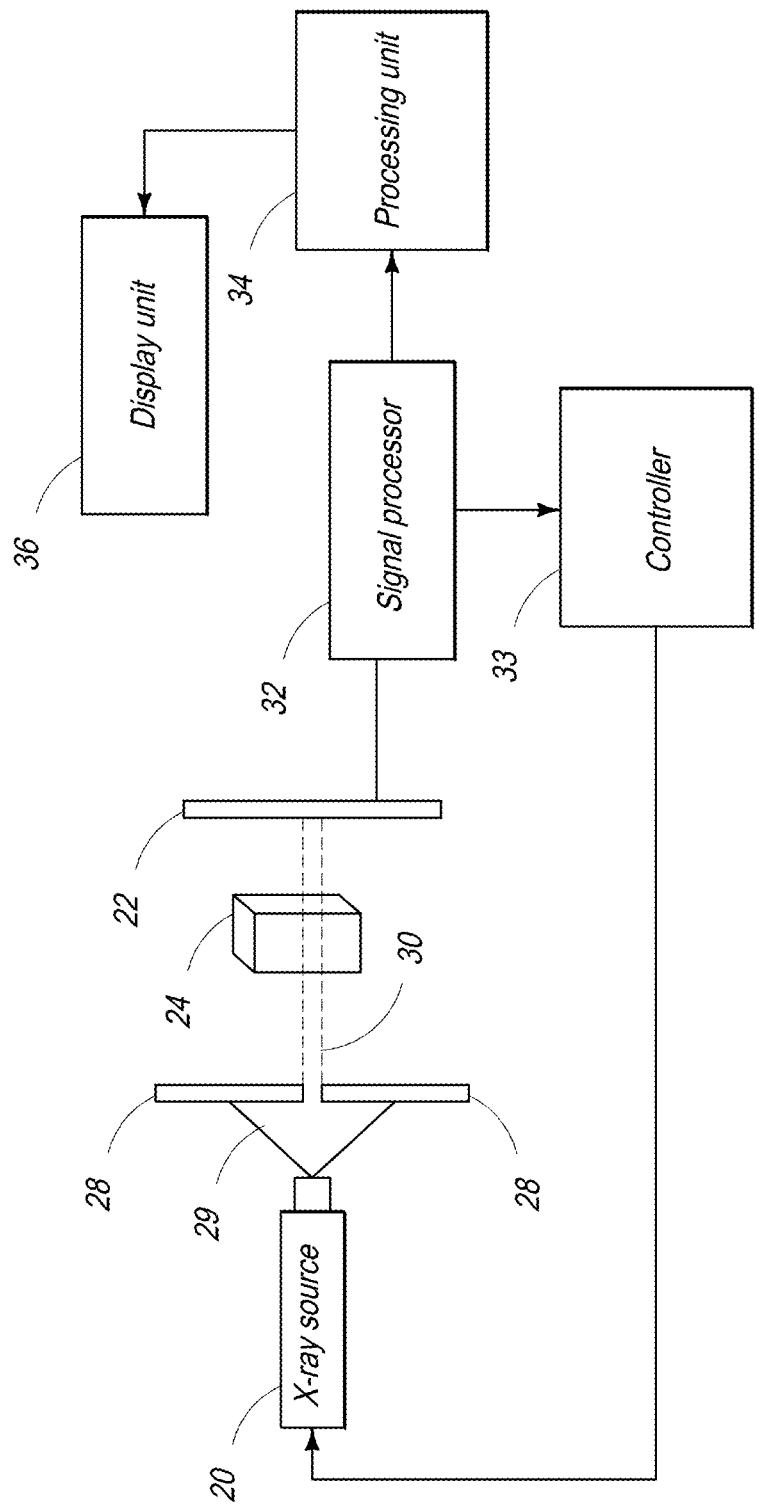
FIG. 2A is a block diagram of an X-ray screening system for inspecting objects which is used for performing noise spectroscopy, in accordance with an embodiment of the present invention.

FIG. 2A is a block diagram of an X-ray screening system for inspecting objects which is used for performing noise spectroscopy, in accordance with an embodiment of the present invention. The X-ray screening system comprises an X-ray source 20 and a plurality of X-ray detectors 22. An object to be inspected 24 is placed between the X-ray source 20 and the detectors 22 so that X-rays generated by the X-ray source 20 pass through the object 24 and impinge upon detectors 22. In one embodiment, the screening system also comprises a collimator 28 which reduces the originally produced cone of X-rays 29 to a fan beam of X-rays 30. The X-ray source 20 may be any X-ray source commonly known in the art, such as an X-ray tube, a linear accelerator of electrons with an X-ray target, or a radioactive source with a suitable energy spectrum. The detectors 22 comprise an array of any of the X-ray detectors commonly used in the art, such as scintillators with photomultiplier tubes or photodiodes, or semiconductor X-ray detectors. The object 24 being scanned may either be moved perpendicularly through the fan beam of X-rays by a conveyor system or the object 24 may be kept stationary and the X-ray source 20, and detectors 22 may be moved to scan the fan beam across the stationary object 24.

The detectors 22 output low-level current signals which are fed to a signal processor 32, which comprises circuitry for signal conditioning and data converters such as analog-to-digital converters (ADC) for achieving a required signal to image the scanned object 24. In an optional embodiment, the X-ray screening system comprises a controller 33 coupled with the signal processor 32, which provides a control signal to the X-ray source 20. X-ray sources, collimators, detectors and components of a signal processor employed with an X-ray inspection system are well known in the art, and in the interest of brevity those details are not described herein. The signal processor 32 processes the signals to produce image data which is fed to a processing unit 34 (computer) for analysis and extraction of information. The image data may be fed to a display unit 36 such as a screen, a video display unit (VDU), a liquid crystal display (LCD), etc., either directly by the signal processor 32 or by the processing unit 34.

It would be appreciated by persons having reasonable skill in the art that the X-ray system described in FIG. 2A may be structurally modified in a plurality of ways such as by adding one or more X-ray sources, detectors, housing, conveyors, processing circuitry, and other ancillary equipment, or altering the positions of any of the components illustrated, without departing from the scope of the present invention.

Further, the X-ray system as illustrated in FIG. 2A may be used in a broad range of applications such as security applications, academic applications, industrial applications, medical applications, etc. The X-ray system may be used for purposes such as screening baggage on airports, inspecting cargo to detect any contraband materials, detecting the presence of nuclear materials and with some structural modifications in medical imaging applications such as Computed Tomography (CT) scanning, scanning materials for defects, weaknesses or deficiencies, or medical applications.

Various applications are described in, for example, U.S. Pat. No. 4,020,346, which is issued to Dennis A. Donald, and describes an "[a]pparatus for the production and visual inspection of the moving fluoroscopic image of an article during movement of said article through said apparatus, comprising a shielded housing, an X-ray exposure station within said housing comprising an X-ray emission station, a fluoroscopic screen shielded against the transmission of X-rays and a baggage inspection station located between said emission station and said screen, said emission station comprising an X-ray emission tube adapted to emit a continuous beam of X-rays of low intensity through said inspection station and onto the surface of said screen, said X-rays being of such low intensity as not to damage photographic film, and a shielded focal member having an opening which focuses all of the X-rays emitted from said emission station as a divergent beams which strikes substantially only the surface of said screen, a television camera adapted to produce video signals corresponding to fluoroscopic images produced on said screen, intensifier means associated with said camera for converting the weak low-intensity X-ray images present on the fluoroscopic screen to video signals which are intensified by a factor of at least about 1000 times gain, a television monitor which is viewable outside said housing by an operator and is associated with said camera and is adapted to receive said intensified video signals and produce intensified television images on said monitor corresponding to the fluoroscopic images present on the fluoroscopic screen, conveyor means for continuously moving an article to be inspected into said X-ray exposure station through an entrance opening in said shielded housing, into said baggage inspection station and out of said shielded housing through another opposed exit opening therein to provide a continuous moving fluoroscopic image of said article passing through said baggage inspection station, sensing means in the area of said entrance opening to sense the entry of an article to be inspected and to activate the X-ray emission tube until a predetermined period of time after the article passes said means, and shielded flexible curtains means covering each of said opposed openings and adapted to retard the escape of X-rays from said inspection station while permitting said article to be conveyed therethrough, said flexible curtain means comprising two spaced banks, each of which comprises two superposed layers of vertically-slit leaded-vinyl plastic, the slits in one of said layers being offset from the slits in the other of said layers.".

Further, U.S. Pat. No. 4,366,382, assigned to Scanray Corporation, describes "[a] system for inspecting objects including an x-ray source, conveyor means for moving said objects through rays in the output of said source, means for receiving said rays after they have passed through said objects, means responsive to the output of said receiving means for providing a video display in accordance with the receiving means output comprising a light-emitting screen in the form of a strip, an array of photo-detectors opposite said screen for generating electrical signals in accordance with the light emission of the portions of the screen thereopposite, separate means for individually integrating the output of each of said detectors, electronic sampling circuit means for time multiplexing the outputs of said integrating means to provide a series of sequential pulses representing the outputs of said integrating means, means responsive to said pulses for generating video output signals, and video monitor means responsive to said video output signals for displaying said video output signals, and means for collimating the rays of said source into a narrow fan-shaped beam prior to their passage through the objects, said beam scanning said objects in successive slices as the conveyor means moves the objects therethrough.".

Still further, U.S. Pat. No. 7,440,544, assigned to Reveal Imaging Technologies, Inc. describes "[a] method for scanning a bag to determine if the bag poses a threat, the method comprising: performing a CT scan of the bag to produce CT scan data; processing the CT scan data to obtain lineogram data; determining measured values for x-ray attenuation and size of a first object in the bag based on the lineogram data; comparing the measured values to predetermined values; if the measured value is below the predetermined value for at least one of x-ray attenuation and size then determining that the object does not pose a threat and clearing the bag; else, determining the center of mass of the first object based on the lineogram data; modifying the lineogram data based on the center of mass of the first object; determining the density of the first object based on the modified lineogram data; and if the density of the first object is not a predetermined value, then determining that the first object does not pose a threat and clearing the bag."

And still further, U.S. Pat. No. 7,522,696, assigned to GE Medical Systems Global Technology Company LLC, describes "[a]n X-ray CT apparatus comprising: an X-ray data acquisition device for acquiring X-ray projection data transmitted through a subject lying between an X-ray generator and an X-ray detector having a two-dimensional detection plane by a helical scan which acquires X-ray projection data, while said X-ray generator and said X-ray detector are being rotated about a center of rotation lying therebetween with said X-ray generator and said X-ray detector moving relative to the subject lying therebetween; an image reconstructing device for image-reconstructing said acquired projection data; an image display device for displaying an image-reconstructed tomographic image; and an imaging condition setting device for setting various kinds of imaging conditions for a tomographic image, wherein said X-ray data acquisition device includes a first device for a high pitch helical scan using a helical pitch capable for scanning a whole heart of the subject within a time of one heart-beat in synchronization with a predetermined phase in one cycle of a cardiac signal of said subject." All of the aforementioned patents, including U.S. Pat. Nos. 4,020,346, 4,366,382, 7,440,544, and 7,522,696, are incorporated herein by reference in their entirety.

In an X-ray scanning system such as the one illustrated in FIG. 2A, a beam of X-rays is generated, usually by a LINAC, during a pulse, with a certain energy spectrum. These X-rays penetrate the materials being scanned and interact, are scattered or are absorbed, as described above. The interactions depend on the X-ray energy and on the atomic number (Z) of the material. Some of the X-rays enter detectors in a detector array arranged at a suitable position and deposit some or all of their energy, whereby the deposited energy is converted to optical photons. Each X-ray that deposits energy produces a significant amount of optical photons. The optical photons transfer energy to electrons (usually called photoelectrons) in a high efficiency photodiode or other photo-detector. There are a large number of resultant photoelectrons for each quantity of energy deposited by an X-ray. Alternatively, in solid-state detectors, such as those that may be fabricated from a number of semiconductor materials, a large number of electron-hole pairs are directly produced by each quantity of energy deposited by an X-ray. The electrons charge a capacitor. An analog to digital converter (ADC) measures the voltage across the capacitor after the X-ray pulse is over.

Conventional X-ray imaging systems integrate over all X-rays that arrive at the detector, such that the transmission measured in the image is a direct measure of the total amount of energy deposited in the detector and not a measure of the individual number of X-rays detected. However, the present invention provides a method of measuring the average energy and number of X-rays detected by analyzing the variances, statistical fluctuations, or 'noise' in the scan image to obtain spectroscopic information about the material being scanned.

The X-ray system illustrated in FIG. 2A is operated to extract spectroscopic information from scan data obtained at the detectors 22 or the signal processor 32 by adding an executable spectroscopy routine, as described herein, that is stored in a memory and, when executed by a processor, analyzes the data to automatically determine the atomic number of the material, and, in one specific embodiment, whether the material under inspection has a high atomic number or a low atomic number. In various embodiments, the spectroscopy routine is stored within or executed by processing unit 34. In accordance with the present invention, processing unit 34 may be a general purpose computing device comprising various types of operating systems, memory configurations and computing platforms, as would be appreciated by a person of skill in the art. In addition, those of ordinary skill in the art will recognize that devices of a less general purpose nature, such as hardwired devices, field programmable gate arrays (FPGAs), application specific integrated circuits (ASICs), or the like, may also be used for processing the spectroscopy routine without departing from the scope and spirit of the inventive concepts disclosed herein.

The methods of the present invention are based on the principle that the number of X-rays that produce a particular signal level in a detector after passing through a material having a high atomic number is greater than the number of X-rays that produce the same signal level in the detector after passing through a material having a low atomic number. This is because the detected signal level is a measure of the total energy of all X-rays contributing to the signal.

Since the mean energy of the X-rays is lower after passing through materials having a high atomic number than after passing through materials having a low atomic number, more individual X-rays contribute to produce the same signal level. A greater number of X-rays contributing to the signal leads to improved X-ray statistics.

Therefore, the methods of the present invention are able to use a value dependent upon, and derived from, characteristics of individual, discrete X-rays and not simply rely on the calculations of total transmitted, and detected, energy.

Figure 2B:
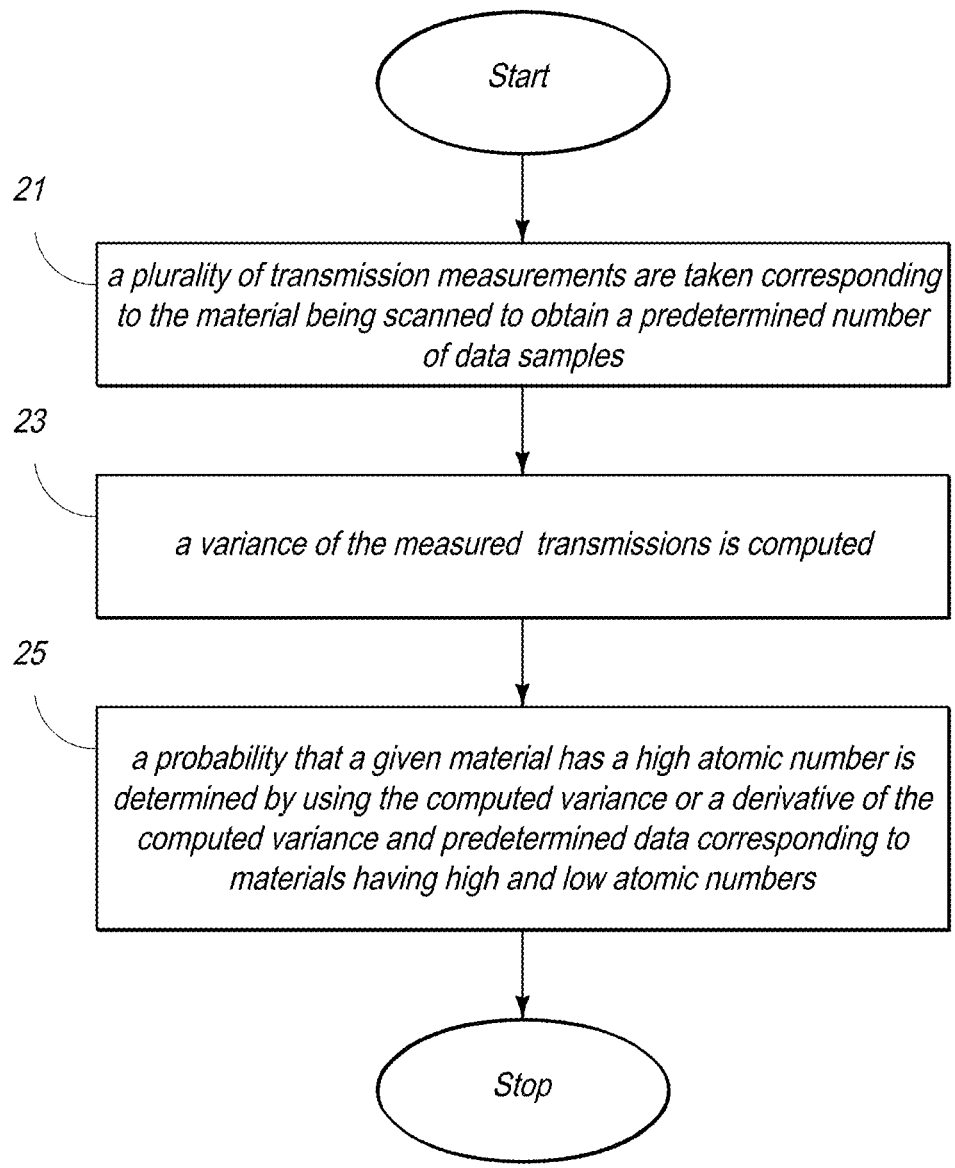
FIG. 2B is a flow diagram of a routine to determine spectroscopic information about a material being scanned by analyzing statistical fluctuations in the scan data.

FIG. 2B is a flow diagram describing a routine used to determine spectroscopic information about a material being scanned by analyzing statistical fluctuations in the scan data. To obtain a predetermined number of data samples, at step 21, a plurality of transmission measurements is taken, corresponding to the material being scanned. At step 23, a variance of the measured transmissions is computed. At step 25, a probability that a given material has a high atomic number is determined by using the computed variance or a derivative of the computed variance and predetermined data corresponding to materials having high and low atomic numbers. Alternatively, the atomic number of the materials is directly computed. Exemplary software systems and methods for determining a variance indicative of the material constitution being scanned will now be described.

First Embodiment

In a first embodiment, the present invention provides an Image-Based Noise Spectroscopy (IBNS) method to obtain spectral information indirectly by analyzing statistical fluctuations (i.e. "noise") in a radiographic image obtained after passage of X-rays through a material being scanned. The spectral information is then interpreted to determine the atomic number, and in one embodiment, whether the material being scanned has a high atomic number or a low atomic number. In IBNS, the principle of the present invention is reflected in the fluctuations around the mean of the transmissions measured in adjoining pixels belonging to the same object. It is observed that after passing through materials having a high atomic number the fluctuations will be smaller than after passing through materials having a low atomic number.

In one example, in order to demonstrate an analysis of statistical fluctuations (i.e. "noise") in a radiographic image obtained after passage of X-rays through a material being scanned, X-rays are passed through a steel plate and a tungsten plate, which are matched in the sense that the mean transmission through the plates is the same. To achieve this matching, the thicknesses of the plates are adjusted accordingly. Transmission is measured by how much energy is deposited in the detector during the pulse, or some other predefined period of time. Since tungsten has a higher atomic number and, therefore, a higher electron-positron pair-production cross section than steel, more high-energy X-rays are lost while passing through the tungsten plate. The mean energy of X-rays arriving at the detector after passing through the tungsten plate is therefore lower than in the case of the steel plate. Since the two plates are matched, however, by varying the thickness of the plate, in order for the plates to yield the same transmission, it is deduced that more X-rays should arrive at the detector behind the tungsten plate than at the one behind the steel plate.

A transmission measurement for the tungsten and steel plates is performed and the transmission values for tungsten and steel are represented as T(W) and T(Fe) respectively. For the measurement through tungsten, the number of X-rays passing from the source through the tungsten plate and arriving at the detector is represented as 'K'. Similarly, for the measurement through steel, the number of X-rays passing from the source through the steel plate and arriving at the detector is represented as 'L'. The transmissions T(W) and T(Fe) are the sums of the deposited energies of the detected X-rays for each measurement and are represented as:

$$T(W) = \Sigma_j E_j(W) = K\mu(W) \text{ where } j=1 \text{ through } K \quad (1a)$$

$$T(Fe) = \Sigma_j E_j(Fe) = L\mu(Fe) \text{ where } j=1 \text{ through } L \quad (1b)$$

where $\Sigma_j$ indicates the sum is taken over index j which labels the detected X-rays, and $\mu(W)$ and $\mu(Fe)$ are the means of the energies $E_j(W)$ and $E_j(Fe)$.

In an experimental setup, the transmission measurements are repeated a number of times, and different values for the transmission are measured because of statistical fluctuations. The statistical fluctuations, or noise, occur due to at least the following two effects: 1) samples are taken from the given energy distributions, and 2) the statistical nature of X-rays arriving at, and depositing energy in, the detector. The fluctuations due to the first effect can be calculated using the Central Limit Theorem, which states that if one takes a set of N samples from any distribution with finite mean $\mu$ and finite variance $\sigma^2$, that set is approximately Gaussian-distributed with a mean $\mu$ and variance $\sigma^2/N$. This implies that the variance in the sum of the samples has variance $N \sigma^2$, but this only applies for the case one always takes precisely N samples. N itself is distributed according to a Poisson distribution.

The variance of such a random sum of random variables can be calculated using the Law of Total Variance, which states:

$$\text{Var}(X) = E(\text{Var}(X|Y)) + \text{Var}(E(X|Y)) \tag{2}$$

with Y being another random variable on the same probability space, E(X) is the expected value of X and E(X|Y) is the expected value of X given a certain value of Y (and similarly for Var(X|Y)). Here we have:

$$\text{Var}(\Sigma_j E_j) = E(\text{Var}(\Sigma_j E_j|N)) + \text{Var}(E(\Sigma_j E_j|N)) \tag{3}$$

This is further represented as:

$$\text{Var}\left(\sum_j E_j\right) = E(N \text{Var}(E_j)) + \text{Var}(N E(E_j)) \tag{4}$$

$$= \text{Var}(E_j) E(N) + \text{Var}(N) E(E_j)^2$$

$$= N\sigma^2 + \text{Var}(N)\mu^2$$

$$= N(\sigma^2 + \mu^2) = N\langle E^2 \rangle$$

where the fact that the Poisson distribution with mean N also has variance N was used. As above, angle brackets denote taking the mean. Note that Equation (4) is also the rule for the variance of the sum of the weights for a weighted histogram, $\text{Var}(\Sigma_j E_j) = \Sigma_j E_j^2 (= N\langle E^2\rangle)$.

The total variances for the two transmissions are then represented as:

$$\text{Var}(T(W)) = K[\mu^2(W) + \sigma^2(W)] \tag{5a}$$

$$\text{Var}(T(Fe)) = L[\mu^2(Fe) + \sigma^2(Fe)] \tag{5b}$$

where the quantities $\sigma(W)$, $\sigma(Fe)$, $\mu(W)$ and $\mu(Fe)$ are the standard deviations (or spreads) and means of the measured distributions as illustrated in FIG. 1A.

In order to determine the smaller variance out of Var(T(W)) and Var(T(Fe)) the following approximation is made. As described in conjunction with FIG. 1A, the square of the mean energy of the X-rays remaining after passing through the tungsten and steel are $\mu^2(W) = 8.12$ MeV$^2$ and $\mu^2(Fe) = 11.02$ MeV$^2$, while squares of the standard deviation of the energy distributions are $\sigma^2(W) = 1.12$ MeV$^2$ and $\sigma^2(Fe) = 1.30$ MeV$^2$ the. Hence, $\mu^2(W) \gg \sigma^2(W)$ and $\mu^2(Fe) \gg \sigma^2(Fe)$. Using the approximation that $\sigma^2$ can be ignored to first order, the variances are represented as:

$$\text{Var}(T(W)) \approx K\mu^2(W) \tag{6a}$$

$$\text{Var}(T(Fe)) \approx L\mu^2(Fe) \tag{6b}$$

Since the W and Fe slabs are matched, the transmissions T(W) and T(Fe) are the same, from which it follows that, on average:

$$K\mu(W) = L\mu(Fe) \tag{7}$$

Equation 7 may also be represented as:

$$K^2\mu^2(W)/[L^2\mu^2(Fe)] = 1 \tag{8}$$

or $$K\mu^2(W)/[L\mu^2(Fe)] = L/K \tag{9}$$

Since L, on average, is smaller than K, the right-hand side is less than 1. Substitution of Equation 6a and 6b into Equation (9) yields:

$$\text{Var}(T(W))/\text{Var}(T(Fe)) \approx L/K < 1 \tag{10}$$

or $$\text{Var}(T(W)) < \text{Var}(T(Fe)) \tag{11}$$

Hence, Equation (11) demonstrates that the variance in the transmissions behind tungsten is smaller than the variance in the transmissions behind steel.

Referring to Equation (5a) and (5b), it is verified that since, in general, both $\mu^2(W)$ is smaller than $\mu^2(Fe)$ and $\sigma^2(W)$ is smaller than $\sigma^2(Fe)$, Equation (11) is further proved. In the specific case illustrated in FIG. 1A, the values of total variances may be determined. Using equations (1a), (1b) and (5a), (5b) it is obtained that: Var(T(W))=3.64×T(W) and Var(Fe)=4.10×T(Fe). Since T(Fe) and T(W) are the same by construction, Var(T(W))<Var(T(Fe)).

Since, in a real world cargo imaging system, the energies of each individual X-ray cannot be determined using conventional detection systems, a second method of calculating variances is applied. A predefined number, N, of measurements of the transmissions $T_i(W)$ and $T_i(Fe)$ through W and Fe is made, where i=1 to N. In an embodiment of the present invention, the transmission measurements are made by analyzing different pixels belonging to the same object in the image. The mean of the measured transmissions for W and Fe is represented as:

$$T_{ave}(W) = \Sigma_i T_i(W)/N \tag{12a}$$

$$T_{ave}(Fe) = \Sigma_i T_i(Fe)/N \tag{12b}$$

The variance in the measured transmissions $T_i$ is then calculated using the following standard equations known from elementary statistics:

$$\text{Var}(T(W)) = \Sigma_i [T_i(W) - T_{ave}(W)]^2/(N-1) \tag{13a}$$

$$\text{Var}(T(Fe)) = \Sigma_i [T_i(Fe) - T_{ave}(Fe)]^2/(N-1) \tag{13b}$$

The variances determined in Equations (13a), (13b) are the same as those determined by using Equations (5a) and (5b). However, Equations (13a) and (13b) can be used in a practical implementation of the method without detailed a priori knowledge of the materials the X-rays pass through.

The Noise Figure Y is now defined as the variance in the transmissions divided by the mean transmission and is represented as:

$$Y \equiv \text{Var}(T)/T_{ave} \tag{14}$$

where Y is only a function of the properties of the sampled energy distributions, which can be demonstrated by substituting Equations (1a), (1b) and Equations (5a), (5b) into equation 14 as:

$$Y = \text{Var}(T)/T_{ave} = [\mu^2 + \sigma^2]/\mu \tag{15}$$

In a special case, where $\sigma$ is small compared to $\mu$ (as is usually the case here), the noise figure Y can be represented as $Y \approx \mu$. In practice, the transmission is measured in arbitrary units, and Y will have an arbitrary scale factor, say, a:

$$Y_{app} \approx \alpha\mu. \tag{16}$$

This approximation may be checked by using the distributions as described in conjunction with FIG. 1A. We find that Y(W)=3.24, $Y_{app}$(W)=2.85, Y(Fe)=3.83 and $Y_{app}$(Fe)=3.32. The relative differences between the Y and $Y_{app}$ are therefore:

$$\Delta Y/Y=[Y(Fe)-Y(W)]/Y(Fe)=0.15 \quad (17a)$$

$$\Delta Y_{app}/Y_{app}=[Y_{app}(Fe)-Y_{app}(W)]/Y_{app}(Fe)=0.14 \quad (17b)$$

It should therefore be apparent that the relative noise deltas are very similar. The difference will depend, in principle, on the Z and the thickness of the material (Equation (17) computes the effect for only two materials at specific thicknesses). On the other hand, Equation (15) can only be used when the variance of the underlying X-ray spectrum is known. While, theoretically, this could be computed (e.g., by simulation) for many materials at many thicknesses, Equation (16) is more convenient for illustrative purposes. In a practical application, the actual variance and mean is computed from the data, and no approximation is used.

Hence, in the IBNS method of the present invention, in order to differentiate two materials by using the variance of their transmissions at a given transmission, either the noise figure, or the variance directly, or the square root thereof, or some other noise variable, is calculated a number of times from different samples by using one or more of the above-mentioned equations. Next, a mean of the calculated values and an error in the mean is calculated. From the computed mean and error, the atomic number of the given material is calculated, or, alternatively, a probability that a given material has a high atomic number is determined, by comparing to predetermined data corresponding to materials having high and low atomic numbers at the given transmission.

Figure 3:
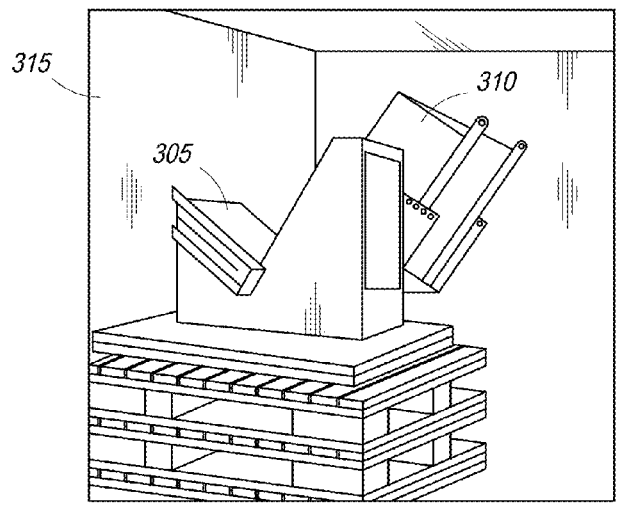
FIG. 3 is an illustration of a setup where lead and steel phantoms are placed in the back of a vehicle.

FIG. 3 shows an experimental setup where lead and steel phantoms, 305, 310 respectively, are placed in the back of a vehicle 315, which also comprises wood cargo.

Figure 4:
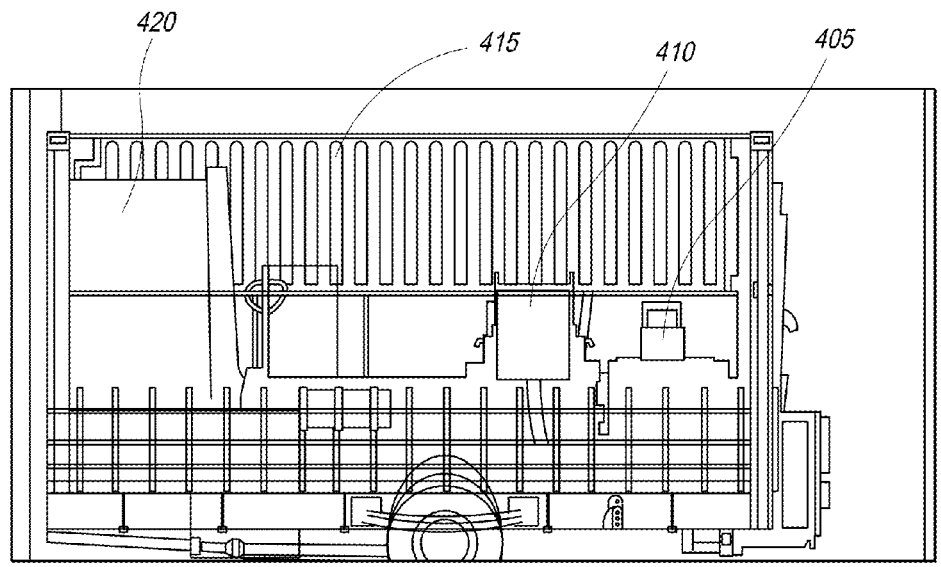
FIG. 4 is a radiographic image of a vehicle in which lead and steel phantoms are placed.

FIG. 4 shows a sample radiography image 400 of truck 415, described and shown in FIG. 3, where area 420 on the left is cargo comprised of wood. The larger object 410 near the center is the steel phantom, and the smaller object 405 to its right is the lead phantom. In this experiment, about ninety radiographic images were taken, with steel thicknesses varying between 0 and 16 inches in 1-2-inch increments, and lead thicknesses between 0 and 9 inches in 0.5-inch increments.

For purposes of analysis, "areas of interest" (i.e. wooden cargo, steel and lead phantoms) comprise 40×30 pixels of the radiographic images. In one embodiment, a moving average of the pixel values is used to determine the signal in each column of 30 pixels in the area of interest, and the differences between it and individual pixel values is used to calculate the variance of the signal. Subsequently, the noise figure is calculated for each column of 30 pixels in the area of interest, and the 40 values are averaged. This is done for each of the three "areas of interest", one for wooden cargo 420, and one each for the steel and lead phantom areas 410, 405, respectively.

It should be noted herein that ninety images were taken in the above example for demonstration purposes, in order to show the effect for different material thickness at high statistical precision.

In a practical commercial implementation of the present invention only one, two, at least two, or more than two images may be acquired. In another embodiment, assume only one image is acquired. A plurality of "sub-areas" or "vertical slices" would then be taken for each "area of interest" in that one image. In other embodiments, a plurality of "sub-areas" or "vertical slices" would be taken for each set of corresponding "areas of interest" in multiple acquired images.

In one embodiment, the plurality of vertical slices refers to the maximum number of vertical slices that can be obtained in that "area of interest", or set of corresponding "areas of interest", presumably belonging to the same object (and, separately, of its surroundings). Note that the term "vertical slice" is used to denote the result of a single X-ray pulse whereby all pixels in the same slice were subject to the same incident x-ray intensity. In a given selected area, the moving average of the pixels in that slice is determined. Further, the statistical fluctuations of individual pixel values from the value of the moving average are also determined. The variance of the statistical fluctuations of individual pixel values and the overall transmission of the average pixel values are also determined, the ratio of which results in the noise figure. This is repeated for the remaining vertical slices. The noise figure is then averaged to determine both the average and the uncertainty of the noise figure. A larger number of slices or sub-areas results in a more precise determination. Therefore, the uncertainty decreases with approximately the square root of the number of slices or sub-areas. If more than one image is obtained, even more noise figures can be averaged, resulting in an improved estimate, with decreasing uncertainty.

Figure 5A:
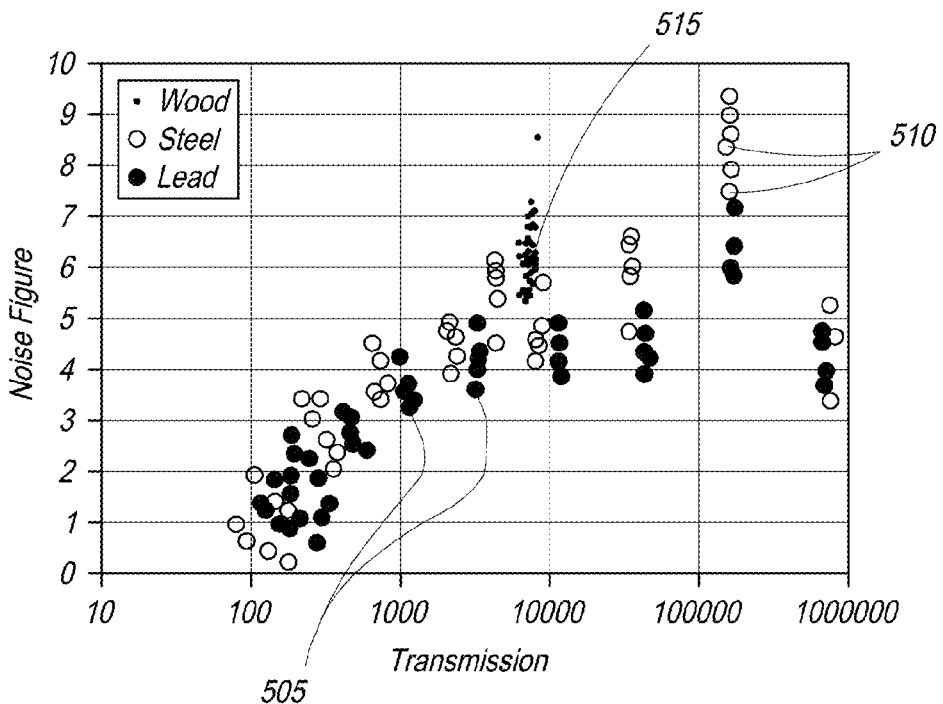
FIG. 5A illustrates transmission-based noise figure plots using image-based noise spectroscopy for the vehicle in FIG. 3 in which lead and steel phantoms are placed.

The noise figure (Y) is plotted with reference to transmission in FIG. 5A. As can be observed from FIG. 5A, the high-Z values (lead) 505 of noise figure are, on the whole, smaller than the low-Z values (steel) 510. Also observable is that for the wood cargo, which has an average Z that is much smaller than for steel, the noise FIG. 515 is higher than that for steel 510.

Figure 5B:
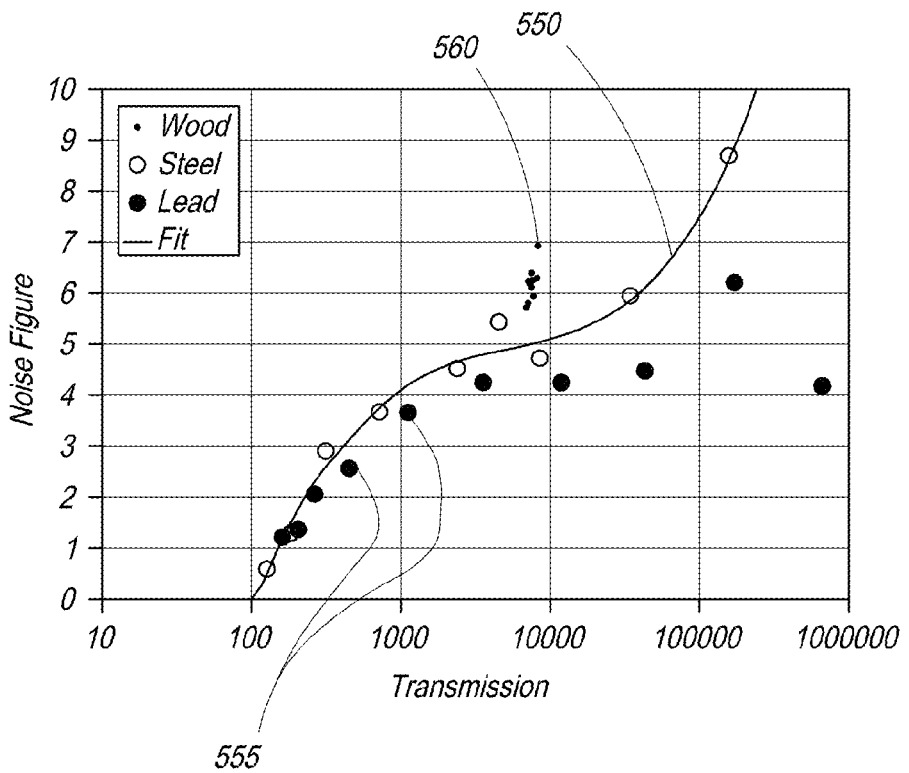
FIG. 5B illustrates transmission-based noise figure plots, averaged over 5 runs, for the vehicle in FIG. 3 in which lead and steel phantoms are placed.

To show this in better detail, FIG. 5B shows the averages of the results of 5 images taken for each cargo configuration, together with a curve-fit 550 to the steel data. There is clear separation between the curve 550 and the lead points 555 below the curve 550, and the wood points 560 above the curve 550.

Second Embodiment

In a second embodiment, the present invention provides an Electronics-Based Noise Spectroscopy (EBNS) method to obtain improved spectral information by applying detection techniques which use X-ray detectors that have a fast response time compared to the X-ray pulse duration, such as fast scintillators (e.g. plastic scintillator, LYSO, $LaBr_3$, or other fast scintillators) or fast solid-state detectors (e.g., CZT, or TlBr, or other fast semiconductor-based X-ray detectors), and fast Analog-to-Digital Converters (ADCs) to analyze statistical fluctuations in the signal as it arrives during an X-ray pulse. In EBNS, the principle of the present invention is reflected in the shape of the signal waveform during each X-ray pulse. Each waveform sample during the pulse may be considered a "sub-pixel" of a pixel in the image. By using advanced electronics to measure both the waveform mean and its spread during each pulse, the presence of material having a high atomic number is positively determined, and specifically, the atomic number of the material can be determined. In one embodiment, additional statistical quantities, such as (but not limited to) skewness and kurtosis, are also calculated and used to aid in the determination.

In EBNS, spectroscopic information is extracted from a plurality of time slices during an X-ray pulse generated in an X-ray scanning system such as that illustrated in FIG. 2A. Within each pixel of a radiographic image, each time slice is equivalent to a separate sub-pixel. A transmitted X-ray spectrum is determined with a high precision by using a predetermined number of sub-pixels. The predetermined number of sub-pixels is dependent upon the X-ray pulse width and the time response characteristics of the detector used. For example, if the pulse width is about 4 μs (which is a common value), and the detector decay constant is about 40 ns (which is the case for LYSO), then the number of slices may be chosen to roughly equal the ratio of the two numbers within a factor of two to three; 4 μs divided by 40 ns is 100, which is roughly the ideal number of slices for this example. Therefore, in this particular case, the number of time slices typically range from 30 to 300, although a lower or higher number of slices may be used. For example, it is possible to take many more time slices, for example 1000 or even 4000, whereby 4000 represents one slice per nanosecond in the given example.

In the latter example provided, wherein a large number of time slices is used, adjacent slices are highly correlated and thus, the difference between two such closely spaced slices will not be a significant indicator of the X-ray noise. It therefore becomes necessary to average a significant number of closely spaced slices so that the correlation between averages of closely spaced slices will be small. Thus, the number of averages of closely spaced slices is preferably in the range of 100 to 300, again referring to the above example. A smaller number of slices leads to smaller correlations between successive slices. However, once the number of slices drops below about 30 slices (in the example), the fact that only a small number of slices is used reduces the statistical power of the measurement. Further, if there are very few X-rays, so that in many slices there is no x-ray at all, then it is advantageous to have a smaller number of slices. In that case, it may also be possible to use standard spectroscopy to measure the individual energy of each X-ray.

Division into sub-pixels using time slices is accomplished by using fast detectors and signal processing electronics, such as ADCs that can sample the X-ray wave form a plurality of times, in the X-ray scanning system and during the X-ray pulse.

Formalisms are derived, as follows, that are used for EBNS analysis of data obtained from experimental setups using different scintillation materials in accordance with various embodiments of the present invention.

Formalism for Signal without Distortion

A measured transmission signal T, as detected by a detector array is given by:

$$T = \alpha E_j E_j = \alpha \mu N \quad (18)$$

where $\alpha$ is a constant associated with the gain of the read-out system, $\mu$ is the mean energy of the X-rays arriving at the detector, and N is the number of X-rays. This assumes that $\alpha$ is independent of $\mu$ and N. The variance of the signal can be computed by the law of total variance and works out to be:

$$\mathrm{Var}(T) = \alpha^2 \Sigma_j E_j^2 = \alpha^2 <E^2> N = \alpha^2(\mu^2 + \sigma^2)N \approx \alpha^2 \mu^2 N \quad (19)$$

Here, $\sigma$ is the standard deviation of the sampled distribution, i.e. the energy spectrum of the X-rays arriving at the detector, and use is made of the approximation that $\mu^2 >> \sigma^2$. Note that the approximate result is also obtained if only fluctuations in N are considered.

Defining the noise figure, Y, as follows:

$$Y \equiv \mathrm{Var}(T)/T \approx \alpha \mu \quad (20)$$

it is observed that determination of Y, in this approximation, yields the mean energy of the X-rays arriving at the detector, aside from a constant factor. The equivalent number of X-rays, N can also be solved using:

$$N = T/Y = T^2/\mathrm{Var}(T). \quad (21)$$

Formalism for Signal with Distortion

A more complicated case arises where the measured transmission depends on N, as modeled below. When bombarded with large numbers of X-rays, the photo-detector used can become saturated. In that case, the measured distorted transmission signal is parameterized as follows:

$$T = \alpha \mu [1 - \exp(-(\beta N)]/\beta \quad (22)$$

which, for small $\beta N$, reduces to Equation 18, but saturates for $N >> 1/\beta$. In Equation 22, $\alpha$ is still a constant, which is now assumed to be independent of N, but may still depend on $\mu$.

Using the approximation in Equation (19) and the fact that $\mathrm{Var}(f(x)) = [f'(x)]^2 \mathrm{Var}(x)$, the fluctuations are now given by:

$$\mathrm{Var}(T) = \alpha^2 \mu^2 N \exp(-2\beta N) \quad (23)$$

The noise figure, Y, then is:

$$Y \equiv \mathrm{Var}(T)/T = \alpha \beta \mu N \exp(-2\beta N)/[1-\exp(-\beta N)] \quad (24)$$

There is no analytic expression for N that does not involve $\mu$. We have:

$$N' \equiv T/Y = [1-\exp(-\beta N)]^2/[\beta^2 N \exp(-2\beta N)] \quad (25)$$

For small $\beta N$, this reduces to N'=N, but, in general, N' is not the number of X-rays contributing to the signal anymore. One can derive an expression for N from Equation 22:

$$N = -\ln[1-\beta T/(\alpha\mu)]/\beta \quad (26)$$

but this expression explicitly contains a $\mu$.

Formalism for Signal with Distortion and Electronics Noise

In a linear approximation, the presence of electronics noise is simulated by adding a constant $\delta$ in Equation 23:

$$\mathrm{Var}(T) = [\alpha\mu\sqrt{N} \exp(-\beta N) + \delta]^2 \quad (27)$$

The noise figure, Y, then is:

$$Y \equiv \mathrm{Var}(T)/T = (\beta/\alpha\mu)[\alpha\mu\sqrt{N}\exp(-\beta N)+\delta]^2/[1-\exp(-\beta N)] \quad (28)$$

N' (as defined in Equation 8) now depends on $\alpha\mu$, but Equation 26 remains valid.

Formalism for Signal for Two Materials

It is possible to attempt to hide a material with, for example, high Z, by placing a large amount of low-Z material in front of, or behind that material. The reason is that large quantities of low-Z material will tend to attenuate the X-ray signal, and therefore the transmission measured in the detector array will be lower than if there were no low-Z material. While the X-ray spectrum is still affected by the high-Z material in such a way as to produce a lower variance, the measured lower transmission will result in an overestimate of the noise figure, since the transmission appears in the denominator in Equation (20). A higher noise figure will give the appearance of a lower atomic number, Z. There is, however, a way to improve the estimate of the noise figure, which is described in the following.

Of necessity, the low-Z material must cover the entire high-Z object in any X-ray radiography image, in order to perform its function. This then requires that a larger extent of low-Z material is used than the extent of the high-Z material. In other words, in the radiography image, the low-Z material (L) will appear to surround the high-Z material (H). To first order, the transmission of the combined (L+H) materials is represented as:

$$T(L+H) = T_0 \exp[-\eta(L)\rho(L)t(L) - \eta(H)\rho(H)t(H)]$$

whereas the transmission of the low-Z (L) material alone is represented as:

$$T(L) = T_0 \exp[\eta(L)\rho(L)t(L)]$$

Here, $T_0$ is the transmission without any material present ("air value"), $\eta$ is the mass attenuation coefficient of the material, $\rho$ the density of the material, and t the thickness. Since, in general, $T_0$ is (or can be) known from measurements, it is possible to reconstruct the transmission due to only the high-Z material in the following way:

$$T(H) = T_0 \exp[-\eta(H)\rho(H)t(H)] = T_0 T(L+H)/T(L)$$

The transmission T(L) and its variance can be directly measured from pixels in the image that are part of the surrounding material. The transmission T(L+H) and its variance for the combined materials can also be directly measured from pixels of the primary object. Thus, the true transmission T(H) can be calculated as explained above. The variance in T(L+H), while not identical to T(H), is dominated by the high-Z material, since the high-Z material is the more restrictive material in terms of allowing high-energy X-rays to pass through. A much improved estimate of the noise figure is, therefore, obtained by using:

$$Y_{improved}(H) \approx \text{Var}(T(L+H))/T(H) =$$
$$= [\text{Var}(T(L+H))/T(L+H)][T(L)/T_0]$$
$$= Y(L+H)[T(L)/T_0]$$

In other words, a better estimate of the noise figure is obtained by scaling its value with the ratio of the transmission of the surrounding material and the transmission "air value". Further improvements may be made by taking the known variance Var(T(L)) into account. Knowing Var(T(L)) allows an estimate of the Z of the L material, which can then be used in a model to estimate its effect on Var(T(L+H)), allowing to solve for a better approximation of Var(T(H)).

Of course, the low-Z material could consist of not just one, but several materials. The discussion above does not significantly depend on the number of materials used, only on their average properties.

More generally, whenever any material is "surrounded" by any other materials, the procedures described herein, or variations thereof, may be used to improve the estimate of the noise figure, or other suitable noise variable.

Experimental Setup and Data Analysis Using EBNS Method of the Present Invention with Plastic Scintillator Detectors In one embodiment of the present invention, plastic scintillator and photo-multiplier tubes (PMT) are used in transmission detectors. In an experimental setup a one-inch diameter, 6-inch long plastic scintillator, with a matching 4-inch-long light guide and a one-inch diameter photomultiplier tube is used in the detector. The detector is inserted in the collimated beam of an X-ray generator, with samples of materials of interest inserted between the detector and the X-ray generator. The pulse length of the particular X-ray generator used in this case is typically between 2 and 2.5 μsec. During the scan, X-ray detector signals are digitized using a commercial one-GSample/sec, 8-bit waveform digitizer card. The digitizer is read out using custom software, producing binary data files containing 50 accelerator pulses worth of data, using 3000 channels for each pulse. Since each channel contains the signal level measured during one nsec of time, the total amount of time recorded, per pulse, is 3 μsec, spanning the 2-2.5-μsec beam pulse.

Figure 6A:
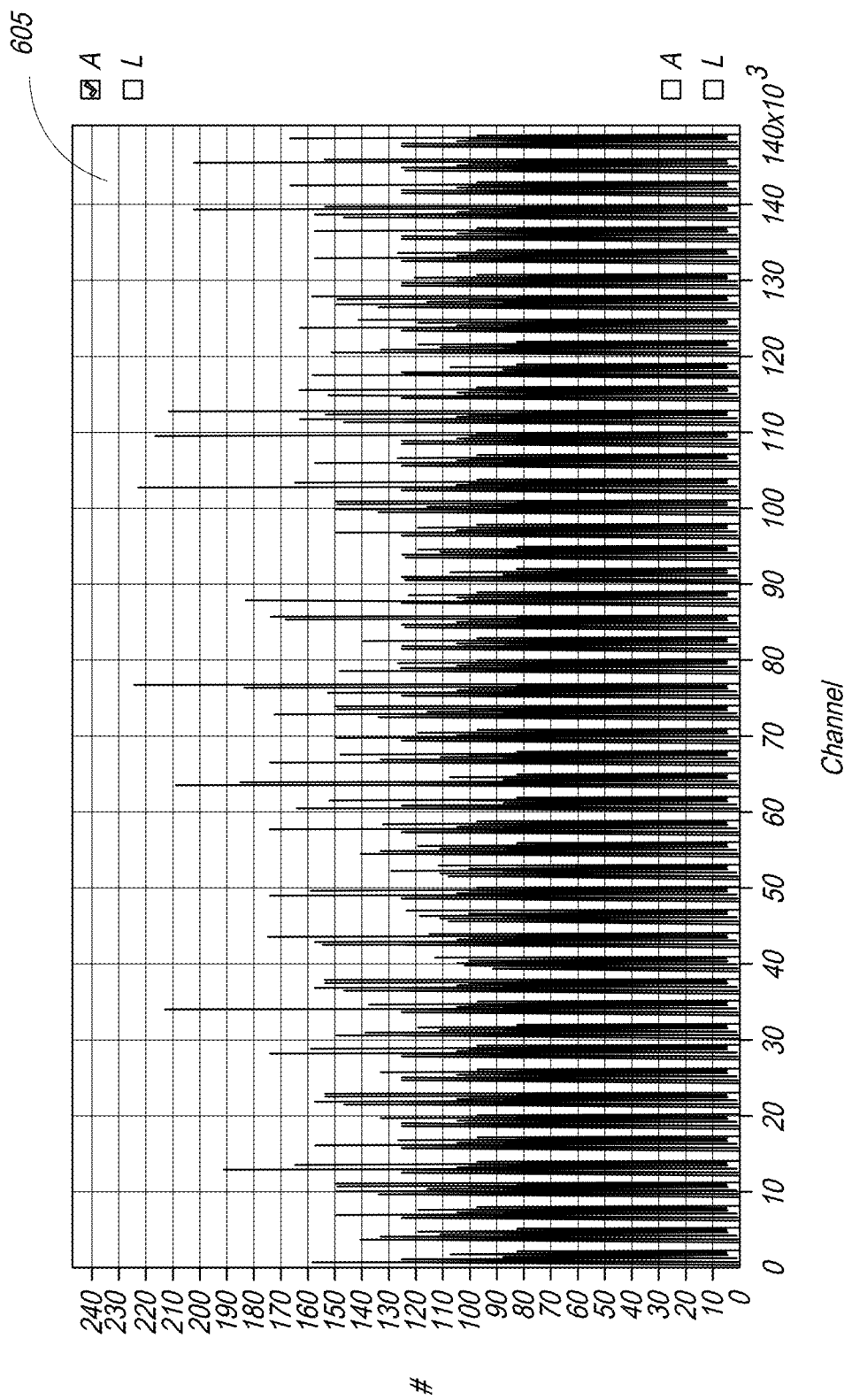
FIG. 6A illustrates exemplary data from one data file (50 X-ray pulses) taken using a plastic scintillator detector with 8 inches of steel in front of the detector.
Figure 6B:
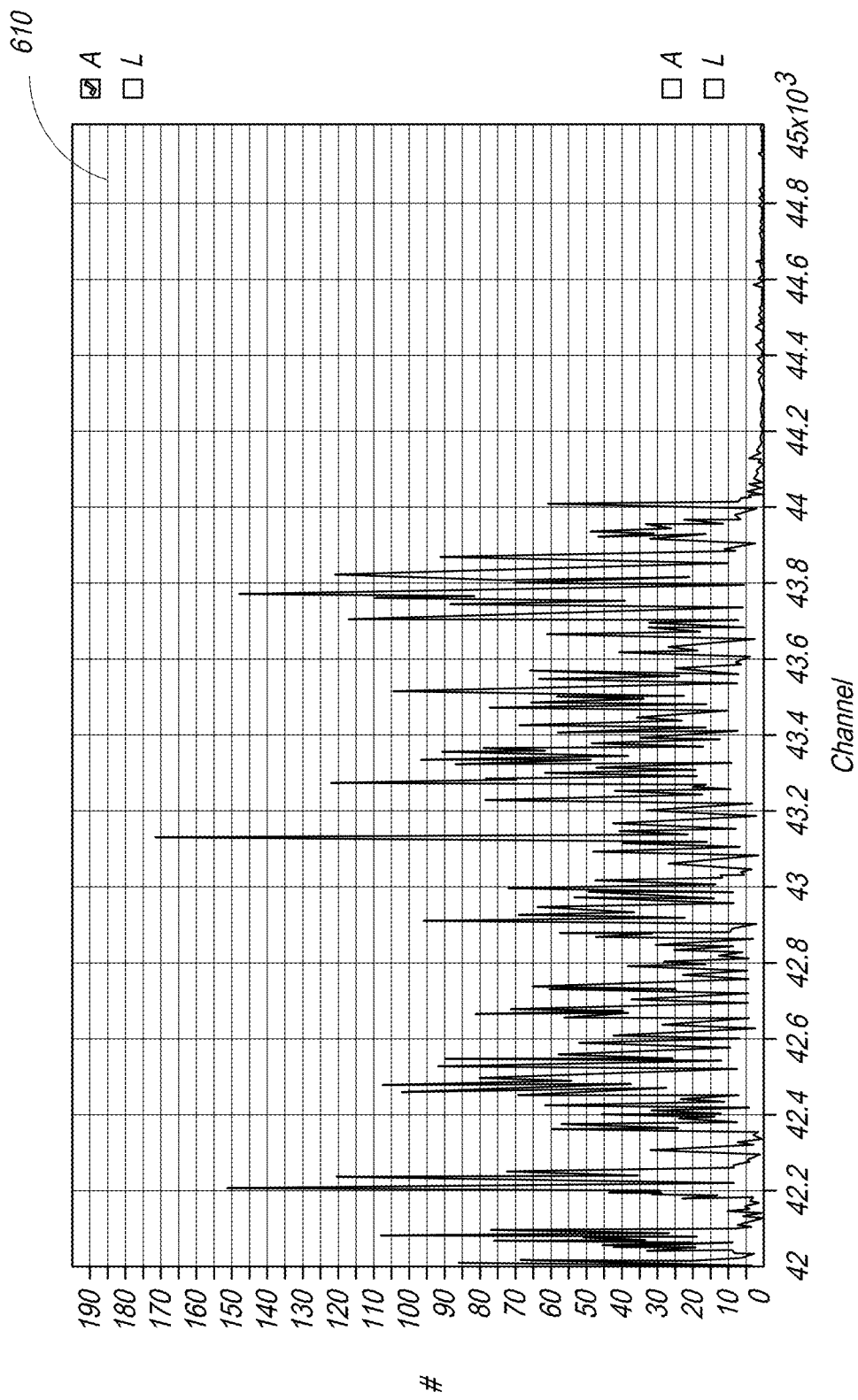
FIG. 6B shows a magnified view of the 15th sample of data from the plot shown in FIG. 6A.

FIG. 6A shows an exemplary data plot 605 from one data file (50 X-ray pulses) taken using the plastic scintillator detector with 8 inches of steel in front of the detector. The data is pedestal-subtracted and converted to positive values. FIG. 6B shows a magnified view 610 of a data plot from the 15th X-ray pulse. As observable from FIG. 6B, the actual length of time during which X-rays are measured in the detector is about 2 μsec. In one embodiment, the data is averaged over 32-nsec intervals, so as to integrate over individual X-ray peaks, thereby leading to 64 time bins, using only the first 2048 nsecs.

Figure 7:
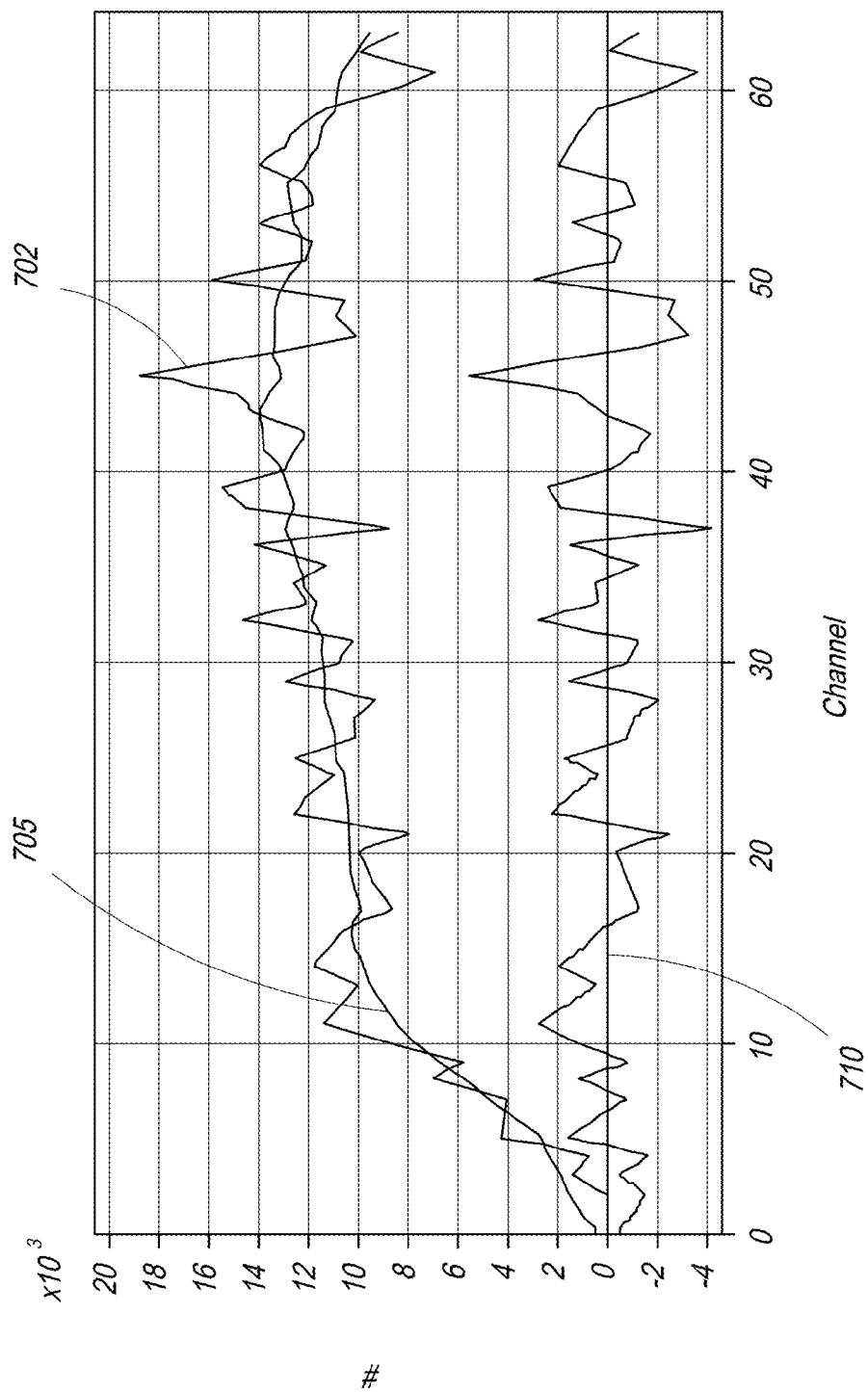
FIG. 7 shows scan data using a plastic scintillator detector, summed over 32 nsec time intervals and corrected for source intensity.

The data used in the current experimental setup is taken with the X-ray source set for a dose of ~100 R/min at one meter. To emulate an actual scan system at full X-ray source power of ~3000 R/min @ 1 m, the experimental data samples are corrected by adding a number of them together. Further, the detector location in an actual scan system will be different from where it is in the experimental setup. In the experimental setup, it is closer to the source than the nominal distance for a typical inspection system. To compensate for both effects, data from 15 pulses are summed for samples taken at 100 R/min @ 1 m, and correspondingly more or fewer for data taken at lower or higher dose rates. FIG. 7 shows the resultant waveform data plot 702 for 8 inches of steel placed in front of the detector.

The variance, V, of the statistical fluctuations is determined using the formula:

$$V = \Sigma(S_i - \langle S_i \rangle)^2 \quad (29)$$

where $S_i$ is the $i^{th}$ sample value in the waveform, $\langle S_k \rangle$ the running average at the $i^{th}$ point and the sum $\Sigma$ is taken across the set of samples. The running average is computed by averaging the sample, its predecessor and its successor together. Curve 705 in FIG. 7 is the running average while curve 710 represents the data with the running average subtracted.

The noise figure, Y, is now computed as follows:

$$Y = V/T \quad (30)$$

with V as computed using Equation 29, and T the total transmission, defined as the integral of the waveform:

$$T = \Sigma S_i \quad (31)$$

Persons of ordinary skill in the art would appreciate that the statistical accuracy of the aforementioned procedure can be improved by using data from an entire object of interest. Therefore, for analysis, the mean noise figure calculated from 25 independent pixels is taken and the error in the mean is used in plots. Similarly, the mean transmission and its error are used. The entire process is then repeated a number of times to simulate different sample objects.

Figure 8A:
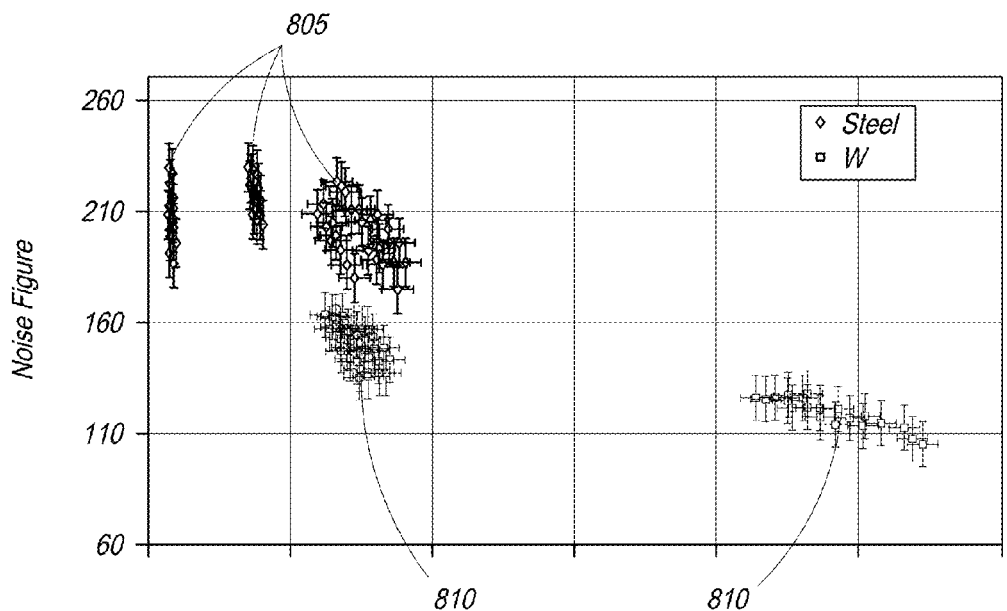
FIG. 8A shows noise figures plotted with reference to an equivalent number of X-rays for steel and tungsten.
Figure 8B:
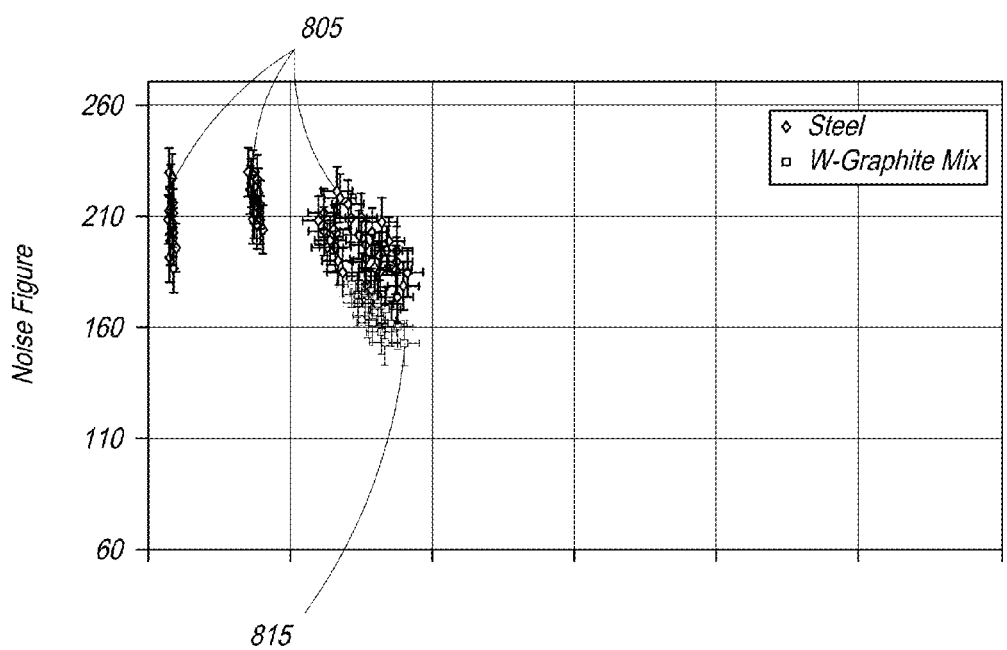
FIG. 8B shows noise figures plotted with reference to an equivalent number of X-rays for steel and tungsten-graphite mixtures.
Figure 8C:
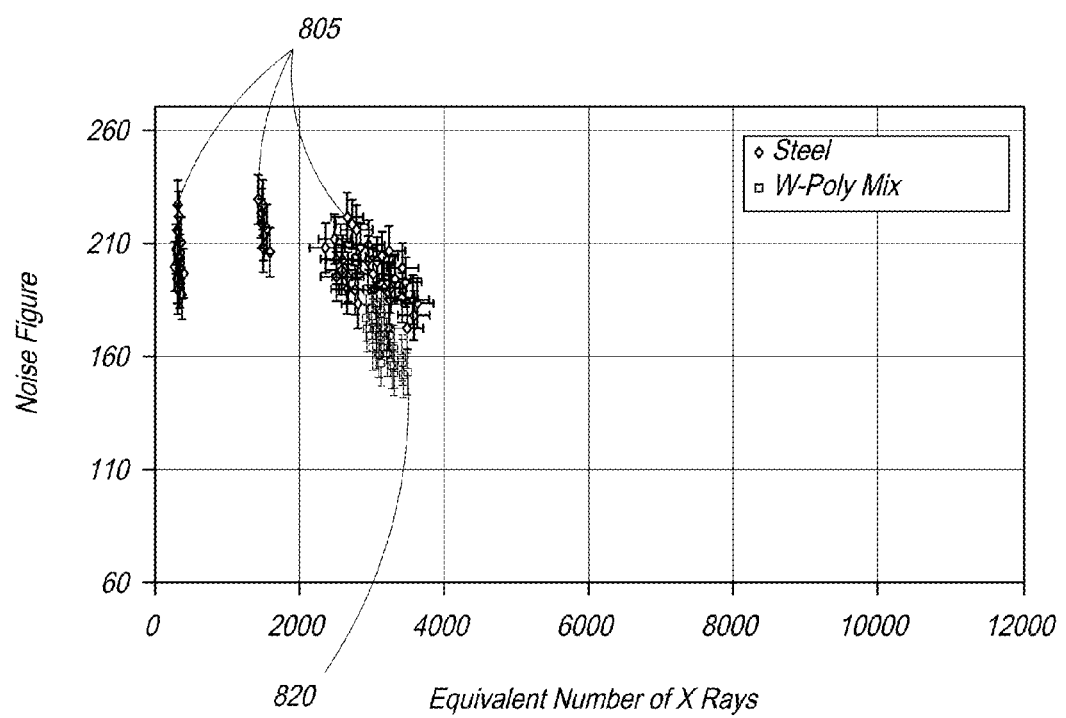
FIG. 8C shows noise figures plotted with reference to an equivalent number of X-rays for steel and tungsten-polyethylene mixtures.

FIGS. 8A through 8C show the noise figure, Y, plotted against equivalent number of X-rays, N, as computed from Equation 21, for multiple sample objects of 25 pixels each and of various thicknesses. N is used rather than another measure of transmission, since N is relatively insensitive to variations in the X-ray-source parameters. FIG. 18A shows results for sample objects of steel 805 and tungsten 810; FIG. 8B shows results for steel 805 and tungsten-graphite mixtures 815, and FIG. 8C those for steel 805 and tungsten-polyethylene mixtures 820. The steel samples have thicknesses of 10, 9, 8 and 7 inches (left to right).

Further, FIGS. 8A through 8C show that Y is less dependent on the equivalent number of X-rays and more dependent on the Z of the material. Specifically, FIG. 8A shows that tungsten 810 is well-separated from steel 805. As admixtures of low-Z materials are inserted, the separation becomes less defined. This is clearly visible in FIGS. 8B and 8C where separation of plots of steel 805 with reference to admixtures of tungsten-graphite 815 (FIG. 8B) and tungsten-poly 820 (FIG. 8C) are less defined.

Figure 9A:
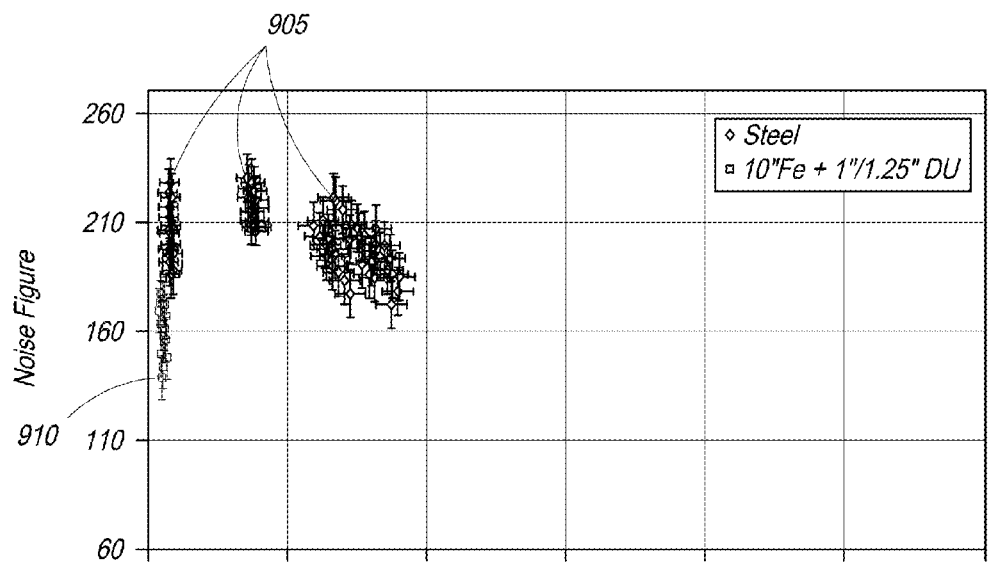
FIG. 9A shows noise figures plotted with reference to an equivalent number of X-rays for steel and depleted uranium with admixtures of steel.
Figure 9B:
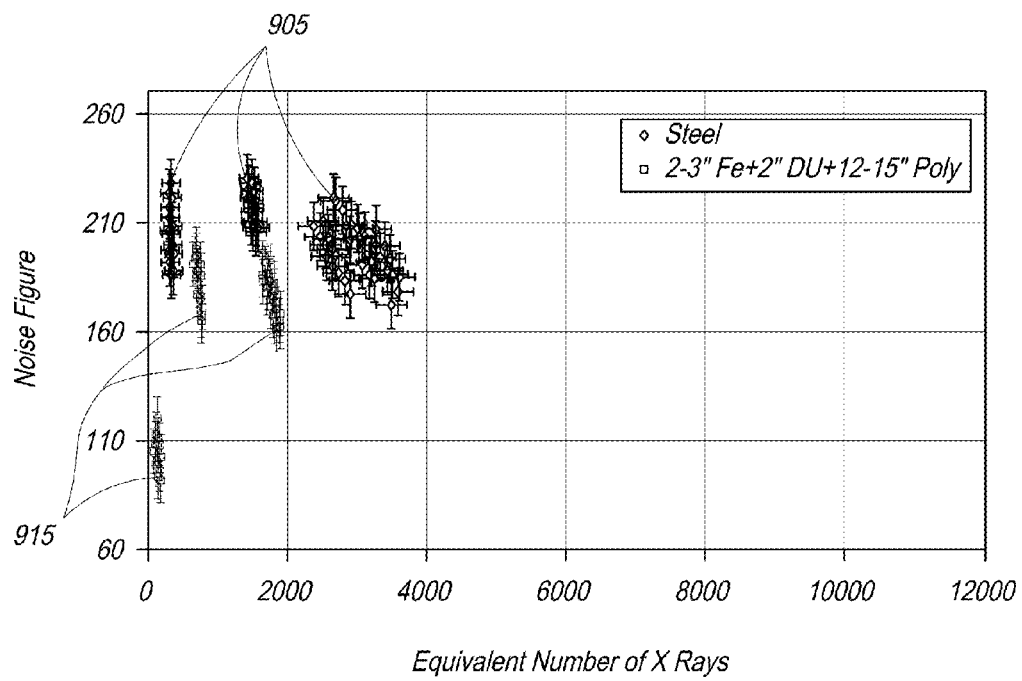
FIG. 9B shows noise figures plotted with reference to an equivalent number of X-rays for steel and depleted uranium with admixtures of steel and polyethylene.

Again, results for the same sample objects of steel and samples of depleted uranium (DU) with admixtures of lower-Z materials are shown in FIGS. 9A and 9B. Specifically, in the plot shown in FIG. 9A, sample data collected from 1 and 1.25 inches of DU 910 together with 10 inches of steel 905 are illustrated. The plot in FIG. 9B shows data from the same steel samples 905, with samples of 2 inches of DU plus 2 to 3 inches of steel plus 12 to 15 inches of polyethylene 915. As is observable from FIGS. 9A and 9B, despite the significant admixture of lower-Z materials, DU is reasonably well separated from steel.

Figure 10A:
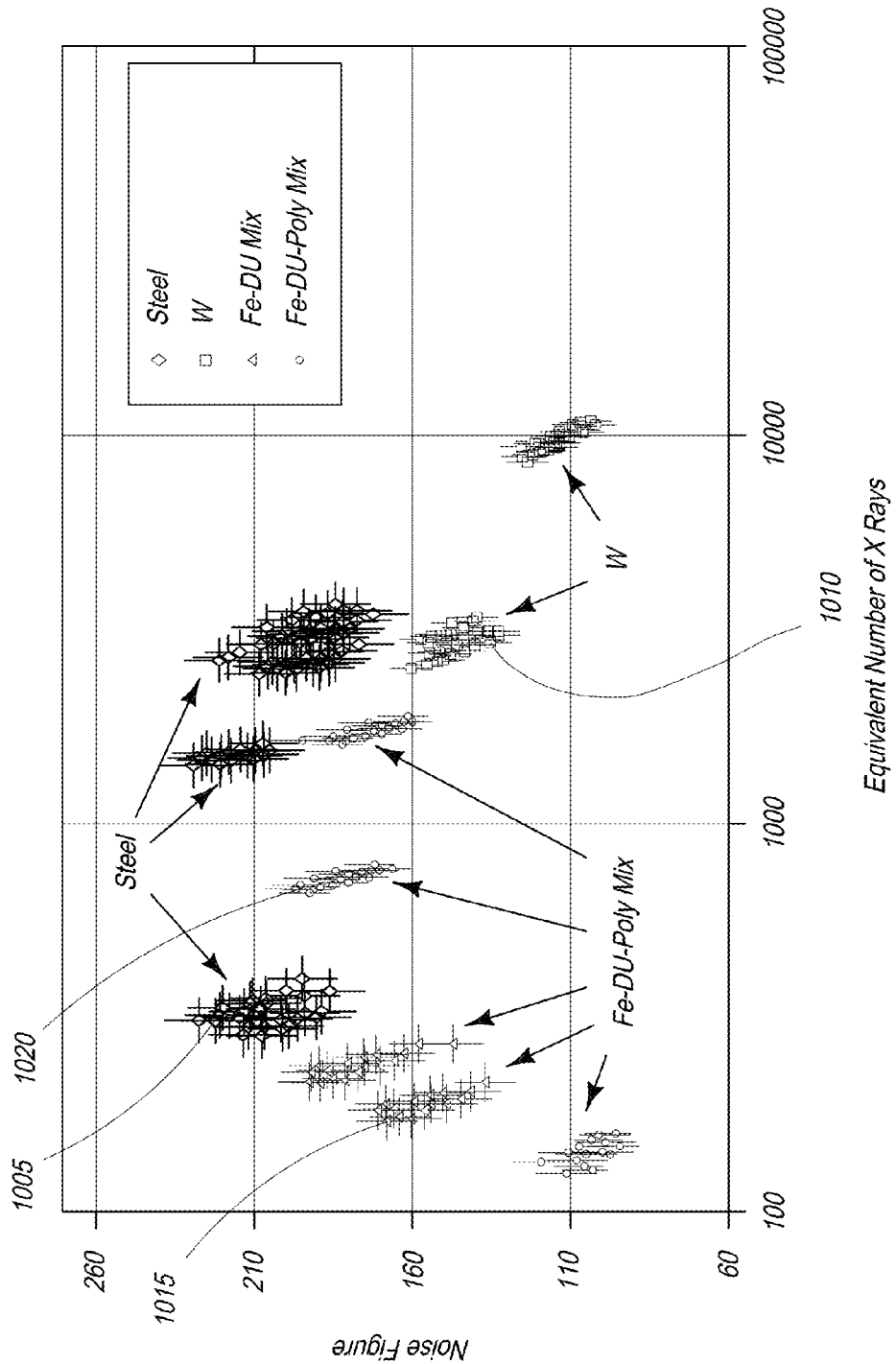
FIG. 10A shows noise figures plotted with reference to an equivalent number of X-rays for steel, tungsten, steel with depleted uranium mixture and steel with depleted uranium and polyethylene admixture.
Figure 10B:
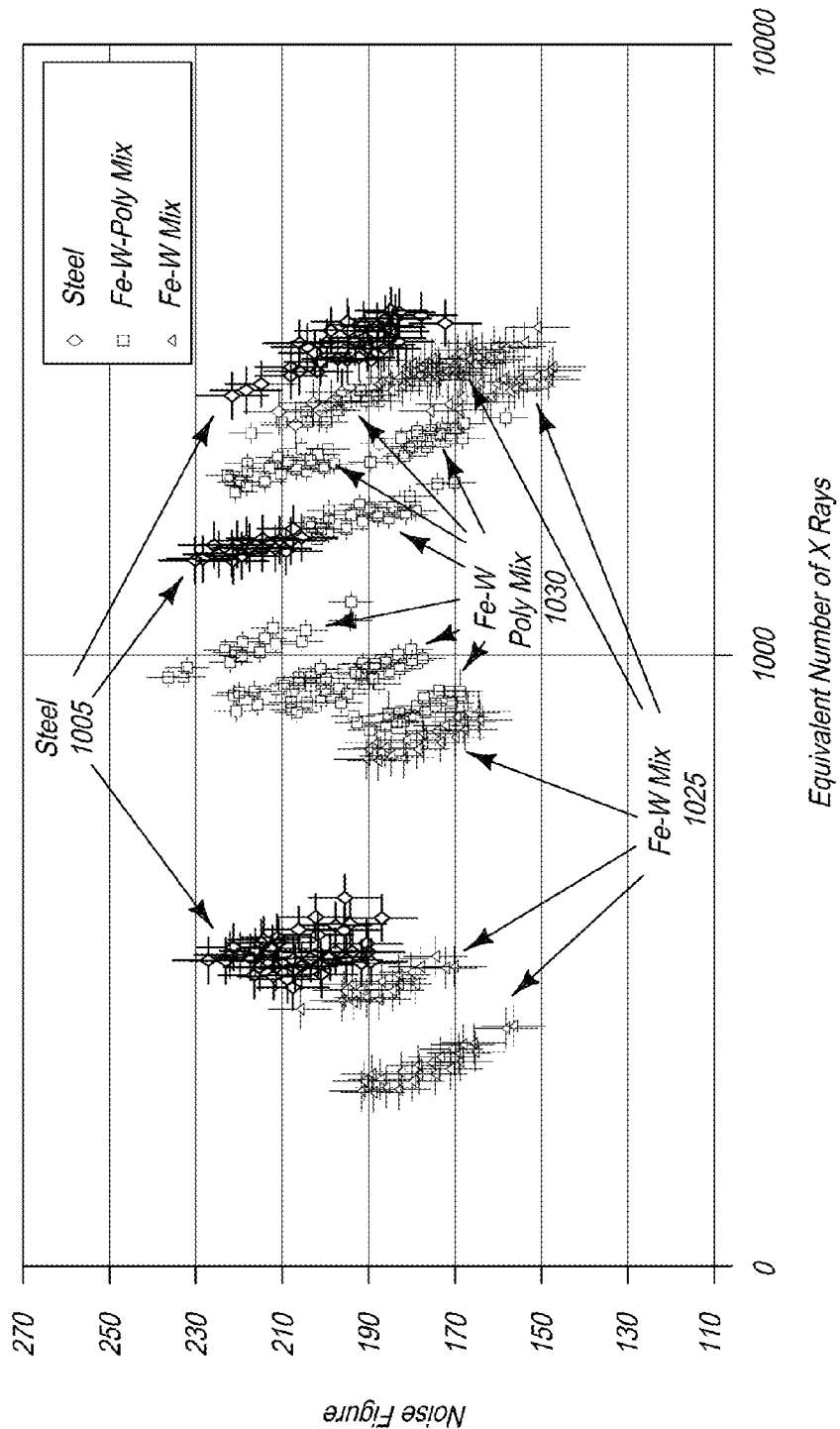
FIG. 10B shows noise figures plotted with reference to an equivalent number of X-rays for steel, steel mixed with tungsten and steel with tungsten and polyethylene admixture.

FIG. 10A shows noise figures plotted against equivalent number of X-rays for sample objects of steel 1005, tungsten 1010 and samples of steel with depleted uranium 1015 and steel with depleted uranium and polyethylene 1020 admixtures. As is observable, steel 1005 is well separated from tungsten 1010. However, with mixtures of steel and depleted uranium 1015 and steel, depleted uranium and polyethylene 1020 this separation becomes less distinct, resulting in overlaps and therefore these represent scenarios of concealing high-Z materials through admixtures of high and low Z materials. Similarly, FIG. 10B shows noise figures plotted against equivalent number of X-rays for sample objects of steel 1005; steel and tungsten 1025; and steel, tungsten and poly admixture 1030. As is observable, there is increased overlap as high- and low-Z materials are mixed. In an embodiment of the present invention, high-Z materials are detectable even when concealed in mixtures of high and low-Z materials (as shown in FIGS. 10A and 10B) since the materials used for concealing high-Z materials typically extend beyond the to-be-hidden high-Z materials and therefore the effect of such camouflaging/surrounding materials can be subtracted to detect the concealed material. In such scenarios the procedures described earlier under section "Formalism for Signal for Two Materials" may be used to improve the estimate of the noise figure.

Experimental Setup and Data Analysis Using EBNS Method of the Present Invention with LYSO Detectors In another embodiment of the present invention, Cerium-doped Lutetium Yttrium Orthosilicate (LYSO) is used as the detector material. LYSO has a decay time of 40 nanoseconds, and therefore, by way of example, for a 4 μsec pulse width, the ideal effective number of independent time slices would be 100.

In another embodiment, a fast analog to digital converter (ADC) delivering, for example, 65 MSamples/sec is used as a signal processing component. The output of the ADCs is processed, using electronic circuitry such as a Field-Programmable Gate Array (FPGA) or ASIC or other computation device. The FPGA computes the total transmission as the sum of the sample values, as well as a noise variable, such as the spread a, or variance, or noise figure Y. In an embodiment, the FPGA also computes other statistical quantities, such as skewness and kurtosis. The computed values corresponding to each detector are then sent to a data acquisition computer. When the data are analyzed by the main system computer, the image is formed as before from the measured transmissions. A segmentation routine finds objects of interest in the image. Using the measured noise variable of a small number of pixels in the object, the mean noise variable is computed with its uncertainty. This mean value of the noise variable is then compared to calibrated values measured previously at the same transmission for high and low atomic numbers. The probability that this object represents a material with a high atomic number is determined, by using the calibrated values, and an alarm is raised if required. More generally, the atomic number of the material can be determined using this technique.

In yet another embodiment of the present invention, the FPGA measures the spread in several sub-segments of the pulse duration, and enables calculation of the mean spread and its uncertainty for a single pixel. In another embodiment, the FPGA sends all sample values to the data-acquisition computer and complex algorithms are used to determine the result. In yet another embodiment, the complex algorithms are implemented directly on the FPGA. In various embodiments, the FPGA reports more than one value to the data-acquisition computer and suitable post-processing of the data is performed to obtain the desired result.

Figure 11A:
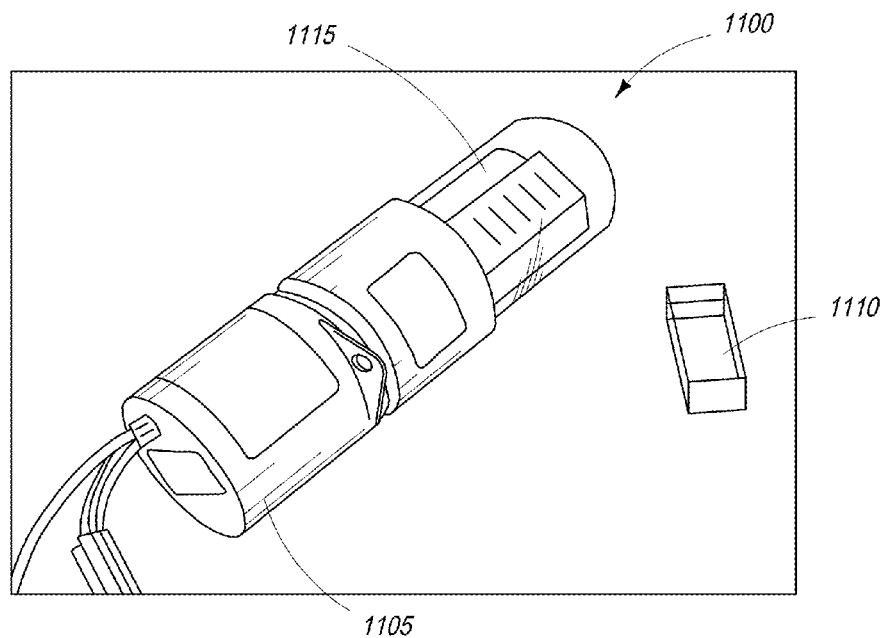
FIG. 11A shows a photomultiplier tube, a base and a LYSO crystal.
Figure 11B:
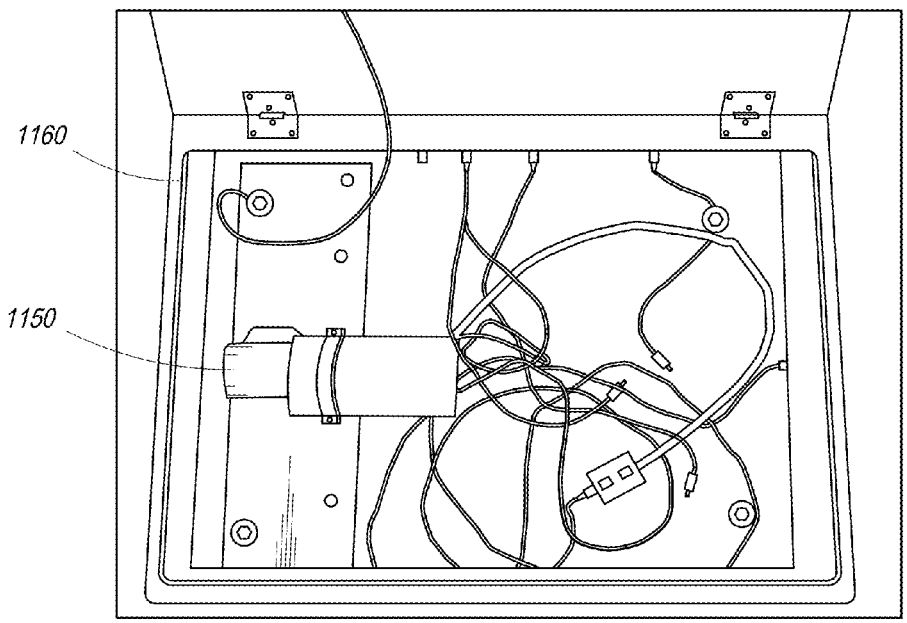
FIG. 11B shows an exemplary LYSO detector, mounted on a photomultiplier tube and housed in a steel box.
Figure 11C:
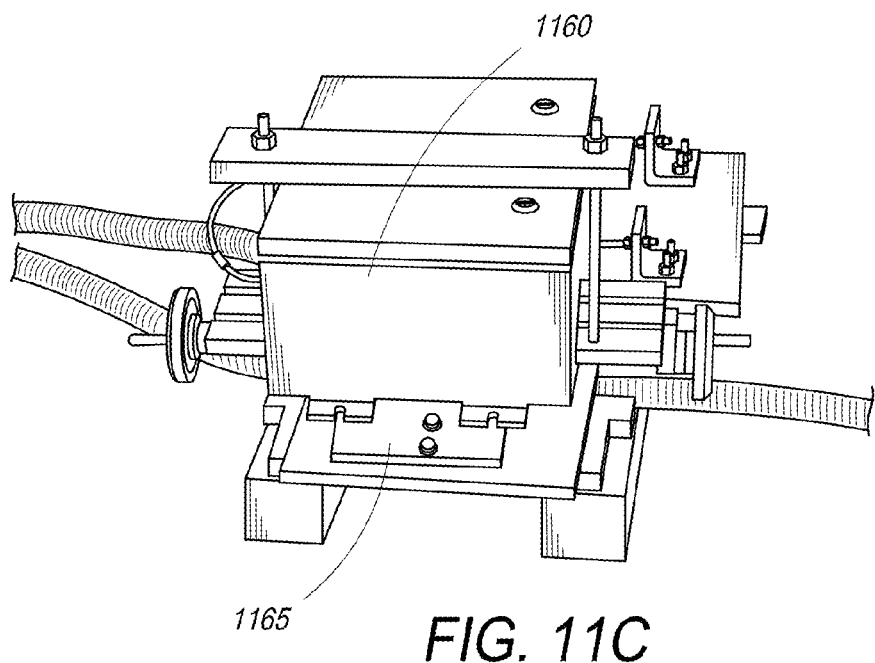
FIG. 11C shows the LYSO detector in a steel box of FIG. 11B, mounted on x-y platform.
Figure 11D:
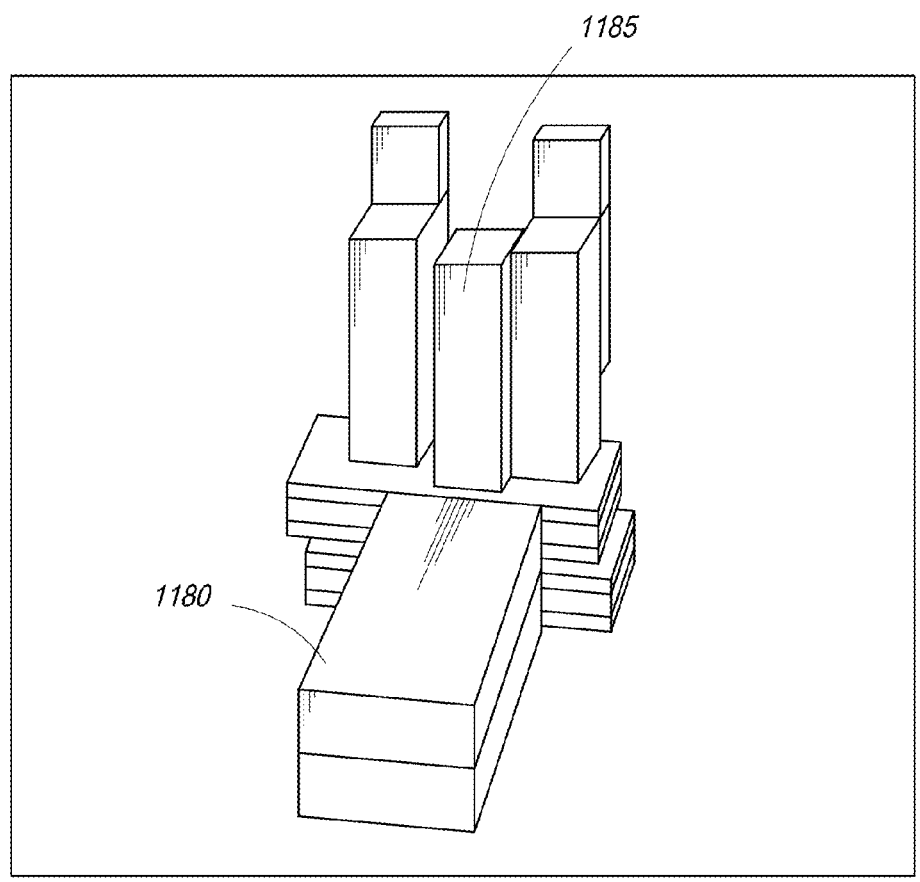
FIG. 11D is close-up view of a 'staging area' in front of the X-ray source for the experimental setup using the LYSO detector, as shown in FIG. 11B.

As shown in FIG. 11A, in one exemplary set-up, a conventional photomultiplier tube 1100, such as but not limited to the RCA 931B, is coupled to an appropriate base 1105, such as but not limited to Hamamatsu HC123-01 base and used with LYSO as a detector material. In one embodiment, a LYSO crystal 1110, having a width of 1.135 cm and a length of 2.5 cm is attached to a side window 1115 of the photomultiplier tube 1100 using Bicron® optical grease, and held in place using a shaped piece of black neoprene. The other five surfaces of the crystal 1110 are wrapped using Tyvek, while ensuring an air gap is maintained. A layer of aluminum foil is used, and, as shown in FIG. 11B, the entire assembly 1150 is then taped. The detector assembly 1150 is then mounted in a steel housing 1160 which is then positioned for scan using an x-y table 1165, as shown in FIG. 11C. A photograph of the entire experimental setup 1170 is shown in FIG. 11D, with a close-up of the 'staging area' 1180 in front of the X-ray source 1185.

A fast analog to digital converter (ADC) is used to read out the LYSO detector and the waveforms are saved out to binary data files. Various thicknesses of steel (3 inches to 16 inches) and lead (1 inch to 9 inches) are put in the 'staging area'. Also, a test run with 2 inches of depleted uranium (DU) is performed. Data is then taken for 5 minutes for each run, using the X-ray source at an intensity of about 100 R/min @ 1 m. All data for this experiment is obtained during the course of a single day, while attempting to keep the X-ray source in the same operating condition as much as possible. Finally, a running average is used to determine statistical fluctuations as described earlier with reference to the experimental setup using plastic scintillator detectors.

Figure 12:
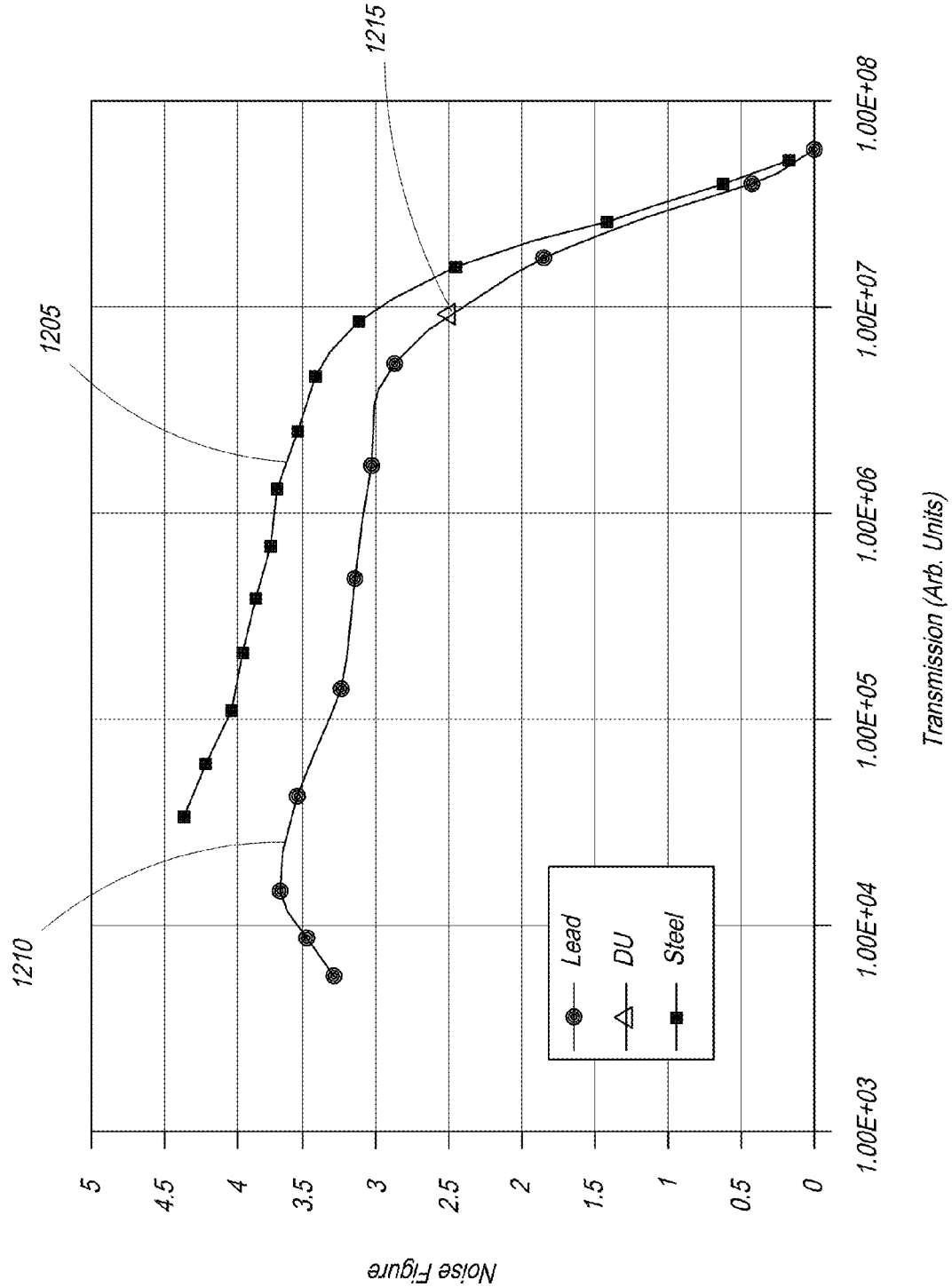
FIG. 12 shows a noise figure plot with reference to transmission (using arbitrary units) for steel, lead and depleted uranium using the LYSO detector.

FIG. 12 shows a plot of noise figure Y with reference to transmission (in arbitrary units). To display the overall trend accurately, high statistics are used for this plot, equivalent to about 500 pixels. As is observable from FIG. 12, lead 1210 has a smaller Y value than steel 1205. The one data point for DU 1215 lies, though within statistical uncertainty, on the curve for lead 1210. Using interpolated versions of the curves 1205, 1210, a normalized noise figure can also be displayed, which is scaled such that the noise figure for steel is constant and equal to 1.

Figure 13:
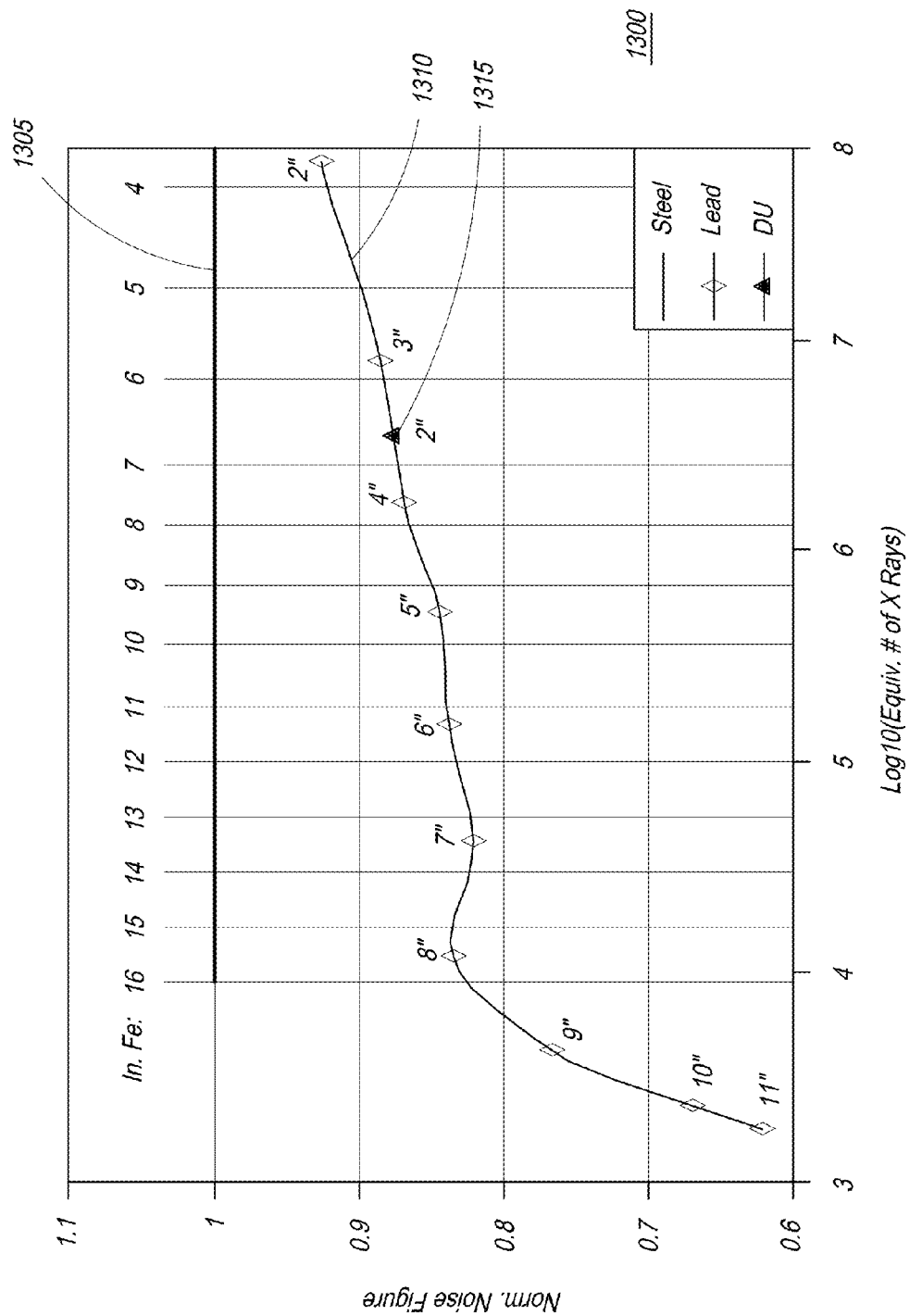
FIG. 13 shows noise figure data of FIG. 12 normalized and plotted with reference to log-base-10 of equivalent number of X-rays.

FIG. 13 shows such normalized results 1300, now plotted with reference to log-base-10 of the equivalent number of X rays, with the material thickness shown for each data point and scaled such that the noise figure for steel 1305 is constant and equal to 1. As is observable, the normalized noise figures for lead 1310 (for various thicknesses) are less than 1, while the normalized data point for DU 1315 lies on the normalized curve for lead 1310.

From Equation 20, described above, it is known that the noise figure is a scale factor, $\alpha$, times the average X-ray energy. In one embodiment, it is assumed that the scale factor is $\alpha=0.85$ while the actual thicknesses of the target materials for each run are known. Therefore after dividing the noise figure by the assumed value for a, the average X-ray energy with reference to sample thickness is plotted in FIG. 14A, for steel 1405 and for lead 1410. The results for lead 1410 are shown in inches of steel-equivalent (SE), by using 1 inch of lead≈1.85 inches of steel. Also shown are results of two simulations representing the average energy of the X-rays detected behind these two materials—simulate steel 1406 and simulate lead 1411. As can be observed from FIG. 14A, there are considerable differences between the simulated results and the data: the measured separation between lead 1410 and steel 1405 is not as large as expected from the corresponding simulations, and there is a significant dip in the data below about 7 inches SE.

Figure 14A:
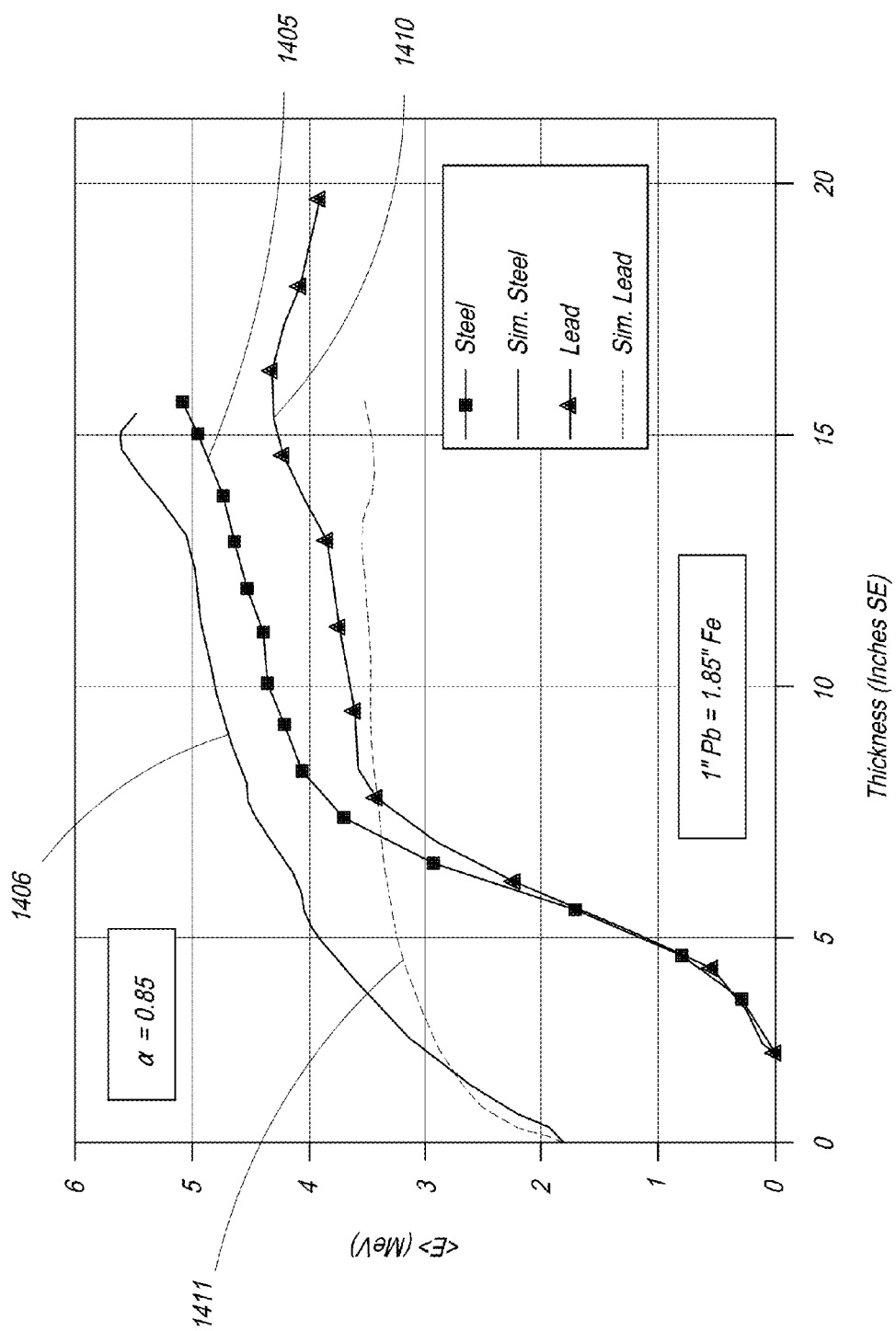
FIG. 14A is a plot of average X-ray energy with reference to sample thickness for steel and lead along with the results of two simulations for the LYSO detector.
Figure 14B:
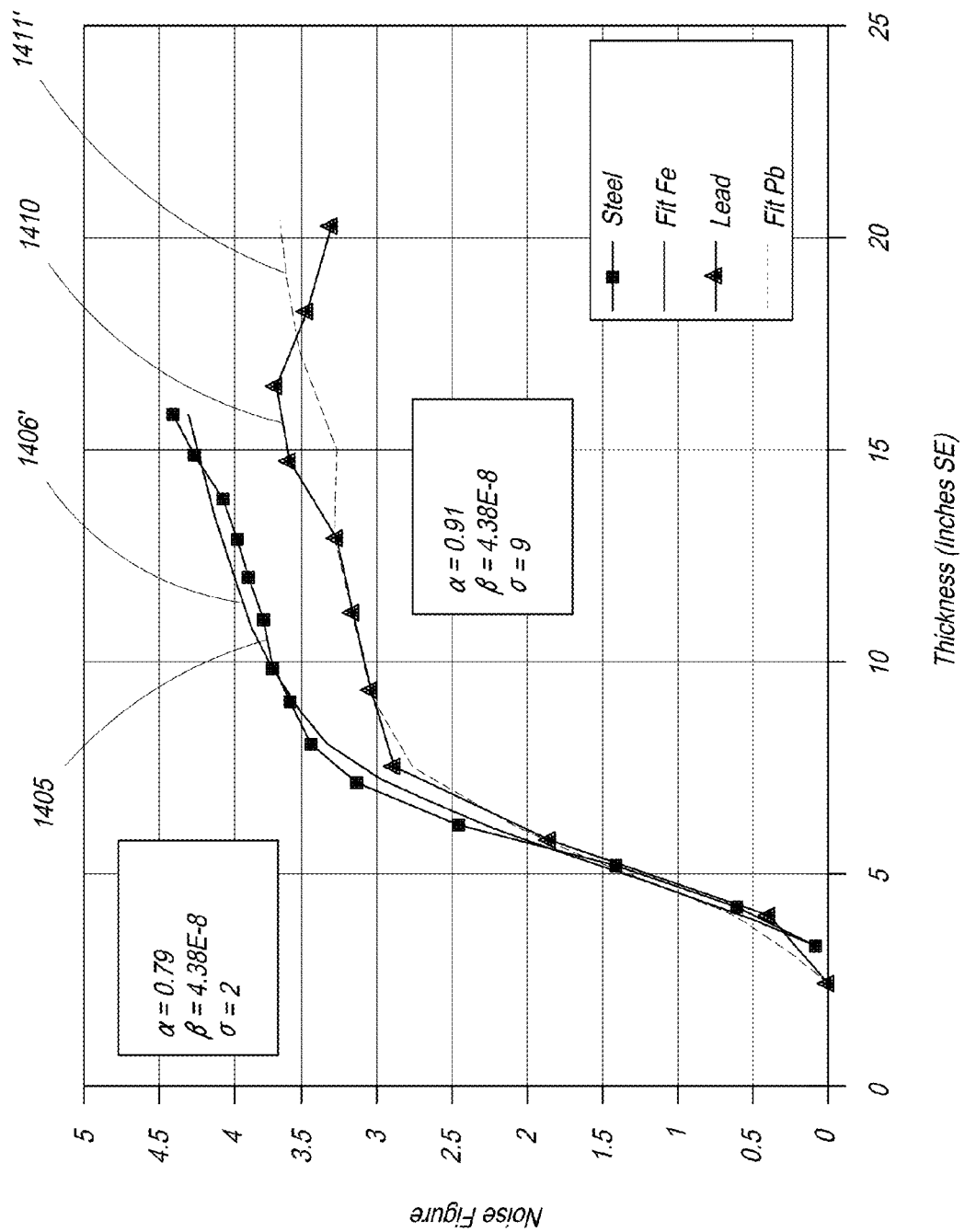
FIG. 14B illustrates the same data shown in FIG. 14A, further showing corrections for the simulation data.

This is attributed to the fact that during experimental measurements a significant amount of non-linearity in the behavior of the photomultiplier tube is present during high-flux measurements. This saturation effect was simulated using the model/equations derived under the sections of "Formalisms for Signal with Distortion" and "Formalisms for Signal with Distortion and Electronics Noise" as described earlier. The noise figures with reference to sample thickness are shown in FIG. 14B, for steel 1405 and for lead 1410 while the simulations are now corrected using the model/equations derived under the sections of "Formalisms for Signal with Distortion" and "Formalisms for Signal with Distortion and Electronics Noise" as described earlier, to have plots 1406' and 1411', as shown in FIG. 14B. Free parameters are the proportionality constant $\alpha$, the saturation parameter $\beta$, and the electronics noise parameter $\delta$. Very good fits are obtained using small values of $\delta$ (2 for steel, 9 for lead), the same value for parameter $\beta(4.38 \cdot 10^{-8})$, and two slightly different values for $\alpha$: 0.79 for steel and 0.91 for lead. The assumed value $\alpha=0.85$, used earlier in FIG. 14A, is the average of these two numbers.

Persons of ordinary skill in the art should appreciate that the reason the two $\alpha$'s are not the same is that Equation 20 is an approximation that avoids the need to know the actual spectral shape for each material and each thickness. In a more careful analysis, the simulations should have been representative of Equation (15) rather than of Equation (20), and closer agreement between the $\alpha$'s would have been obtained.

Another, smaller, contribution comes from the fact that it was tacitly assumed that $\alpha$ is a constant. In reality, a contains the detector efficiency, which is a function of X-ray energy. Since detector efficiency is higher for low-energy X-rays than for high-energy X-rays, the efficiency (and therefore a) behind lead would be higher than behind steel, since the average X-ray energy behind lead is smaller than behind steel. The electronics noise $\delta$ is very small, and, in one embodiment, could be set to 0 without significantly affecting the results.

Figure 15:
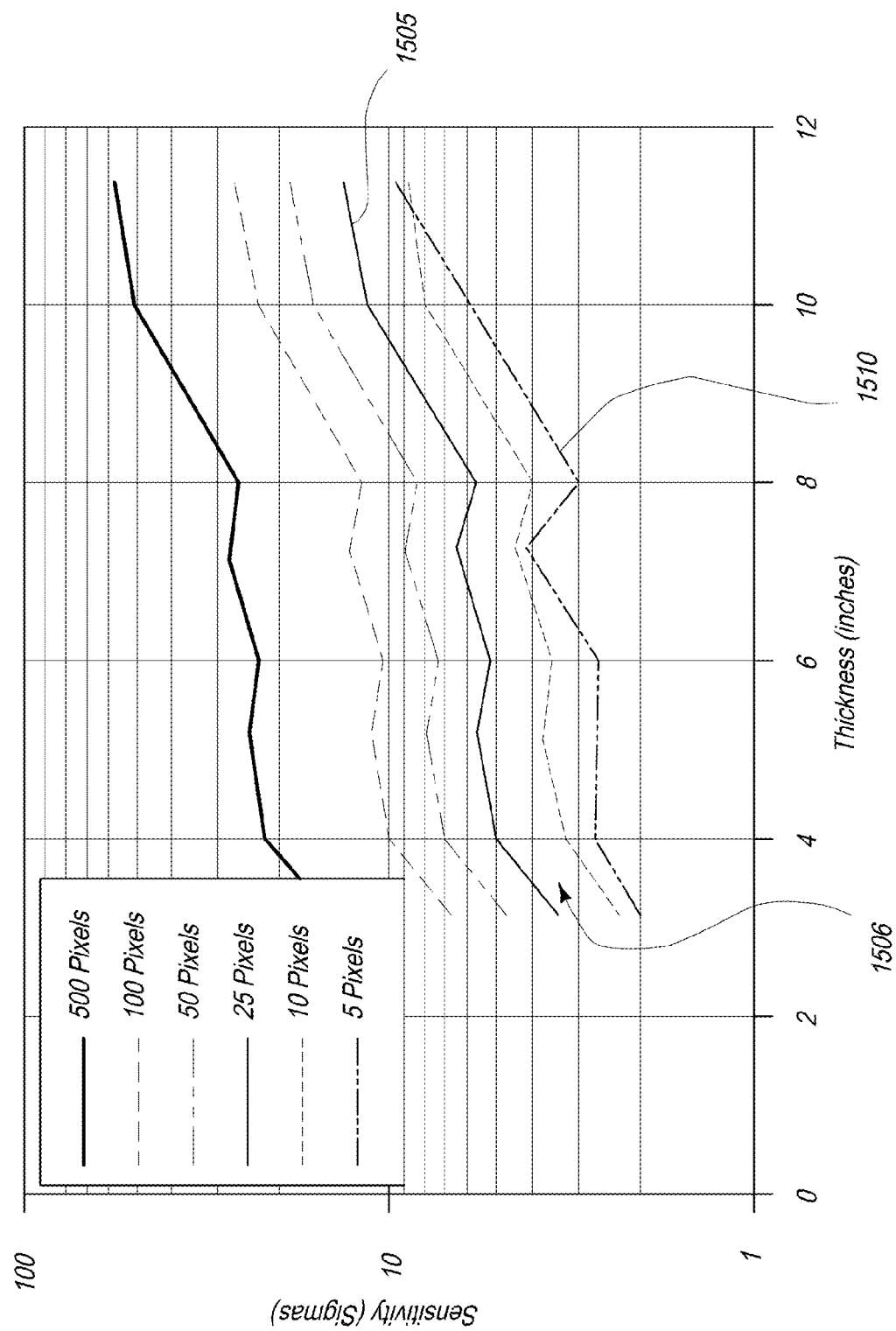
FIG. 15 shows sensitivity of the EBNS method of the present invention as a function of material thickness.

The sensitivity of the EBNS method of the present invention is shown as a function of material thickness in FIG. 15. For a given number of pixels in an object, the differences of the noise figures of steel and lead are shown in terms of the overall uncertainty of the measurement (in sigmas), as a function of material (here lead) thickness. As an example, the separation of lead and steel, using 25 pixels, is given by the curve 1505. At 4 inches of lead thickness, the separation is five sigmas as shown by arrow 1506. Even using only 5 pixels, as shown in curve 1510 the separation is still about 3 sigmas. Generally, the separation improves as the thickness increases. The experimental results therefore show that the EBNS method of the present invention, using LYSO, enables distinguishing between low- and high-Z materials, with reasonably high sensitivity.

Determination of the Atomic Number, Z, from the Noise Variable

In an embodiment of the present invention, to determine the atomic number of an unknown material/object, test phantoms are made from materials of different Z, and, at each Z, of different thicknesses, covering the range of Z and transmission values expected to be encountered in the operation of the scanning system, such as the system of FIG. 2A. Aforementioned test phantoms are scanned in the X-ray beam of the inspection system and the noise variable and transmission for each phantom is measured using the procedures outlined herein. A calibration dataset is produced in this manner both for IBNS and EBNS. Alternatively, or in addition, simulations may be performed for phantoms of different Z and for other thicknesses, and the results of the simulations may be integrated into the calibration dataset. From the calibration dataset, calibration curves may be produced, wherein, for example, the material Z is plotted against the noise variable, each curve at a different transmission value. Persons of ordinary skill in the art will appreciate that it is then possible to use the calibration curves to determine the Z of the unknown object, for example by interpolation, given the measured (and, if necessary, corrected) values of transmission and noise variable for that object. It should be appreciated that the above is only an example of a procedure, and that other procedures and variations can be used as would be advantageously evident to persons of ordinary skill in the art.

The method of noise spectroscopy may be used in a plurality of scanning applications, wherein the inspected material affects the inspection system's primary inspection medium, which may be X-rays, optical photons, etc. The affect must be material specific. For example, it could depend on the material's atomic number, Z, or on one of the material's optical transmission properties. Further, the affect must have a reasonably simple form. For example, it could be monotonous with inspection medium energy or wavelength. Also, the detector employed in the scanning application must be sensitive not just to the presence of the inspection medium, but rather to the inspection medium's affected property, such as energy or wavelength, or a proxy thereof, such as deposited energy. Exemplary applications of the methods of the present invention are described herein with respect to high-energy X-ray radiography of cargo containers and trucks. Another exemplary application of the method of the present invention is in low-energy x-ray baggage scanners.

While some exemplary embodiments of the present invention are described and illustrated herein, it will be appreciated that they are merely illustrative. It will be understood by those skilled in the art that various changes in form and detail may be made therein without departing from or offending the spirit and scope of the invention.

We claim:

1. A method of differentiating among a plurality of areas of interest in an image wherein each area of interest comprises a matrix of C columns and R rows of pixels, the method comprising:

for each of said plurality of areas of interest, using a specially programmed computer to calculate an average of pixel values to determine a signal in each column of R pixels;

determine a variance of the signal wherein the variance is determined by calculating a difference between the average and R pixel values to yield R calculated differences, squaring each of said calculated differences to yield a sum of squared differences, summing said squared differences to yield a sum of squared differences, and dividing said sum by R number of pixels;

calculate a derivative of said variance for each column of R pixels to yield C number of derivative values for the C columns of pixels;

calculate an average derivative value of the C number of derivative values; and using said specially programmed computer, differentiating areas of interest with high atomic numbers from areas of interest with low atomic numbers by comparing the average derivative values of each of said plurality of areas of interest and determining atomic numbers of areas of interest with high atomic numbers by comparing average derivative values of said areas of interest with high atomic numbers to one or more predetermined average derivative values.

2. The method of claim 1, wherein the one or more predetermined average derivative values are derived by generating radiographic images of a plurality of reference materials, wherein a portion of said plurality of reference materials has high atomic numbers and wherein a portion of said plurality of reference materials has low atomic numbers.

3. The method of claim 1, wherein said derivative of variance is a noise figure determined by dividing the variance in R pixel values by a mean of R pixel values.

4. A method of differentiating among a plurality of areas of interest in a radiographic image wherein each area of interest comprises a plurality of vertical slice of pixels, the method comprising:
for each of said plurality of areas of interest, using a specially programmed computer to calculate an average of pixel values, comprised in each of said plurality of vertical slices, to determine a signal in each of said plurality of vertical slices;
determining a variance of the signal wherein the variance is determined by calculating a difference between the average and the pixel values, comprised in each of said plurality of vertical slices, to yield calculated differences in each of said plurality of vertical slices, squaring each of said calculated differences to yield a sum of squared differences in each of said plurality of vertical slices, summing said squared differences to yield a sum of squared differences in each of said plurality of vertical slices, and dividing said sum by the number of pixels in each of said plurality of vertical slices;
calculating a derivative of said variance for each of said plurality of vertical slices to yield a plurality of derivative values for the plurality of vertical slices;
calculating an average derivative value from said plurality of derivative values for the plurality of vertical slices; and
using said specially programmed computer, to differentiate areas of interest with high atomic numbers from areas of interest with low atomic numbers by comparing the average derivative values of each of said plurality of areas of interest and determining atomic numbers of areas of interest with high atomic numbers by comparing average derivative values of said areas of interest with high atomic numbers to one or more predetermined average derivative values.

5. The method of claim 4, wherein the one or more predetermined average derivative values are derived by generating radiographic images of a plurality of reference materials, wherein a portion of said plurality of reference materials has high atomic numbers and wherein a portion of said plurality of reference materials has low atomic numbers.

6. The method of claim 4, wherein said derivative of variance is a noise figure determined by dividing a variance in the pixel values of a vertical slice by a mean of pixel values of the vertical slice.

7. The method of claim 4, wherein said plurality of vertical slices of pixels is defined by a maximum number of vertical slices that can be obtained in each of said plurality of areas of interest.

8. The method of claim 4, wherein all pixels in each vertical slice of said plurality of vertical slices are subject to a same incident X-ray intensity of a single X-ray pulse.

9. A method for determining an atomic number of a first material, wherein the first material is concealed using a combination of a plurality of materials, the method comprising:
obtaining at least one X-ray transmission image of the first material and the combination;
determining a transmission value, representing the combination, from pixels that represent part of the combination in the at least one X-ray transmission image;
determining a transmission value and variance, representing both the first material and the combination, from pixels that represent the X-ray transmission image of both the first material and the combination wherein the variance is determined by:
obtaining an average energy of a plurality of measured transmitted X-rays,
calculating a difference between an energy for each of said plurality of measured transmitted X-rays and said average energy to yield a plurality of calculated differences,
squaring each of said calculated differences to yield a plurality of squared differences,
summing said squared differences to yield a sum of squared differences, and
dividing said sum by a predetermined number of samples;
obtaining a transmission value, representing air, without any material or combination present;
determining a transmission value, representing the first material, using:
a transmission value representing the combination,
a transmission value representing both the first material and combination, and
a transmission value representing air;
determining a noise variable representing the first material; and
determining an atomic number of the first material by comparing a noise variable corresponding to the first material with a reference value.

10. The method of claim 9, wherein the noise variable is determined based upon the variance representing both the first material and combination and the transmission value representing the first material.

11. The method of claim 9, wherein said plurality of materials of said combination comprise at least two materials, wherein one of said at least two materials is a high atomic number material while another of said at least two materials is a low atomic number material.

* * * * *